United States Patent [19]

Goodenough et al.

[11] Patent Number: 5,412,703
[45] Date of Patent: May 2, 1995

[54] REDUCED PARTIAL VOLUME ARTIFACTS IN IMAGE RECONSTRUCTION, WITH APPLICATION TO X-RAY COMPUTED TOMOGRAPHY

[75] Inventors: Davil J. Goodenough, Myersville, Md.; Warren S. Edwards, Burnaby, Canada

[73] Assignee: Institute for Radiological Image Science, Inc., Myersville, Md.

[21] Appl. No.: 13,589

[22] Filed: Feb. 4, 1993

[51] Int. Cl.$^6$ ............................................. G01N 23/083
[52] U.S. Cl. ............................................. 378/8; 378/4; 378/901; 364/413.18
[58] Field of Search ................ 364/413.18; 378/4, 8, 378/901

[56] References Cited

U.S. PATENT DOCUMENTS

| | | | |
|---|---|---|---|
| 5,079,699 | 1/1992 | Tuy et al. | 364/413.22 |
| 5,241,576 | 8/1993 | Lonn | 378/19 |
| 5,253,171 | 10/1993 | Hsiao et al. | 364/413.19 |

*Primary Examiner*—Paul M. Dzierzynski
*Assistant Examiner*—David Vernon Bruce
*Attorney, Agent, or Firm*—A. Sidney Johnston

[57] ABSTRACT

An apparatus for correcting an X-ray tomographic image is presented, where the tomographic image is created by measuring an X-ray transmission coefficient at each of a plurality of X-ray beam paths through an object to enable reconstructing a tomographic image of the object. There is a device for selecting a plurality of volume averaged voxels along at least one of the X-ray beam ray paths, and for placing contiguous volume averaged voxels in a run length of volume averaged voxels, to make a plurality of run lengths of volume averaged voxels. There is a device for dividing the plurality of run lengths of volume averaged voxels into a plurality of subslices. There is a device, responsive to the plurality of subslices and responsive to the plurality of run lengths of volume averaged voxels, for computing a corrected value of X-ray attenuation coefficient for the X-ray beam ray path. There is a device for reconstructing a correction image using the corrected X-ray attenuation coefficient for each X-ray beam ray path. Finally, there is a device for obtaining an improved image by combining the tomographic image with the correction image.

14 Claims, 12 Drawing Sheets

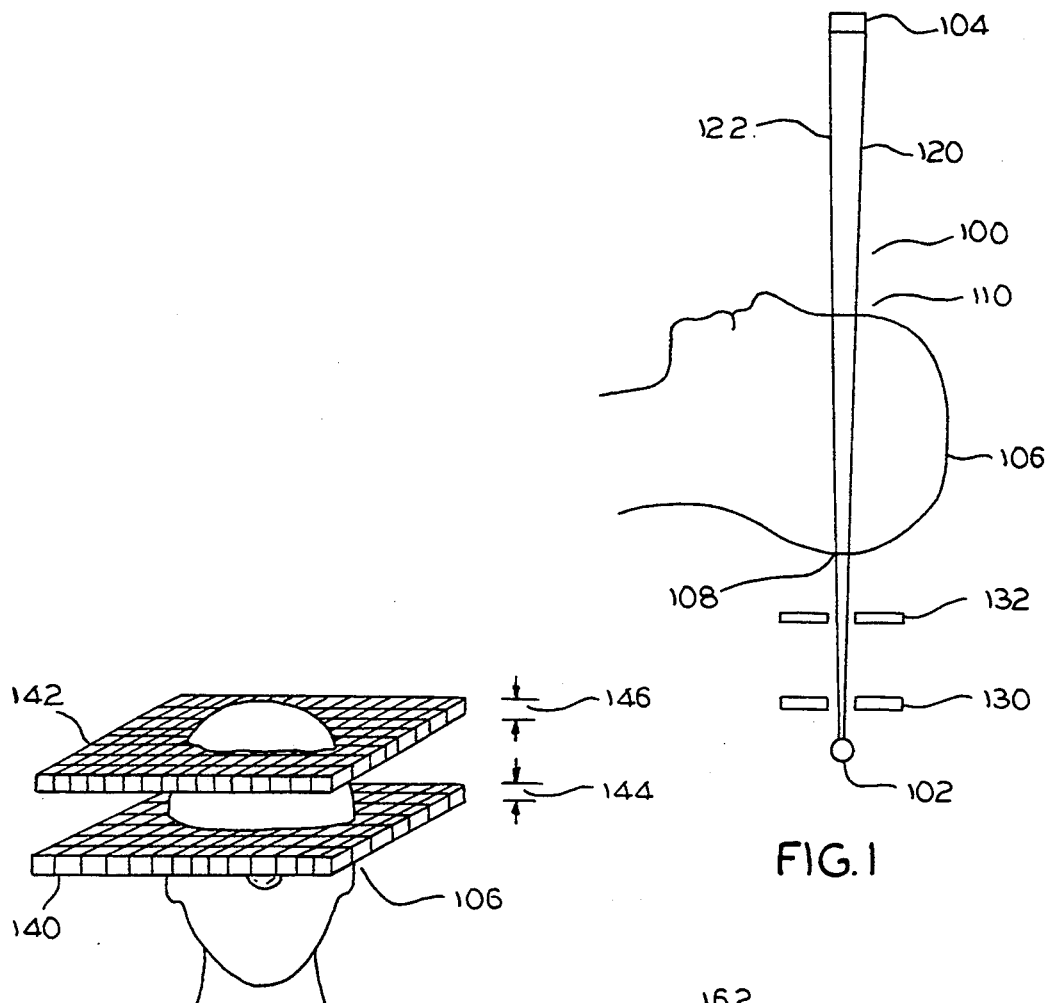
FIG. 2
FIG. 1
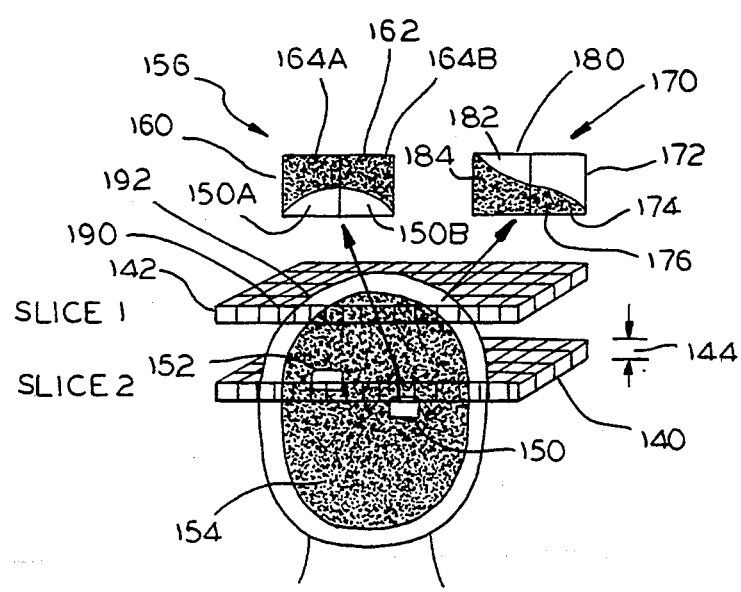
FIG. 3

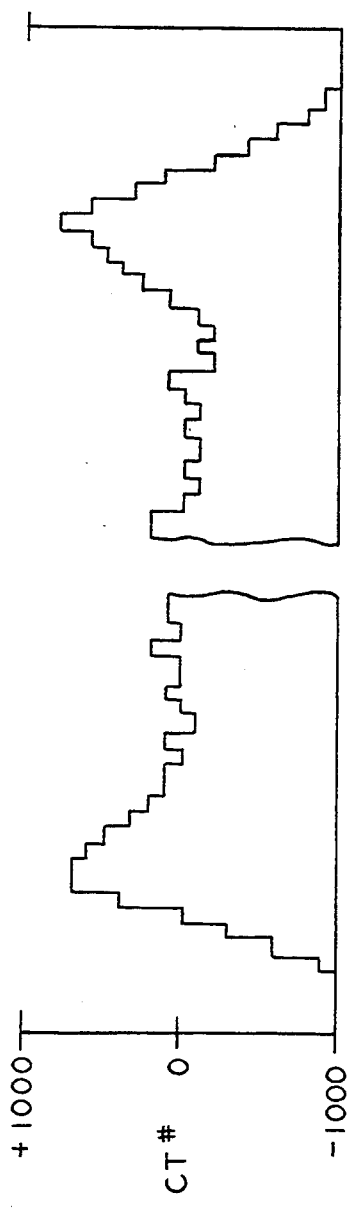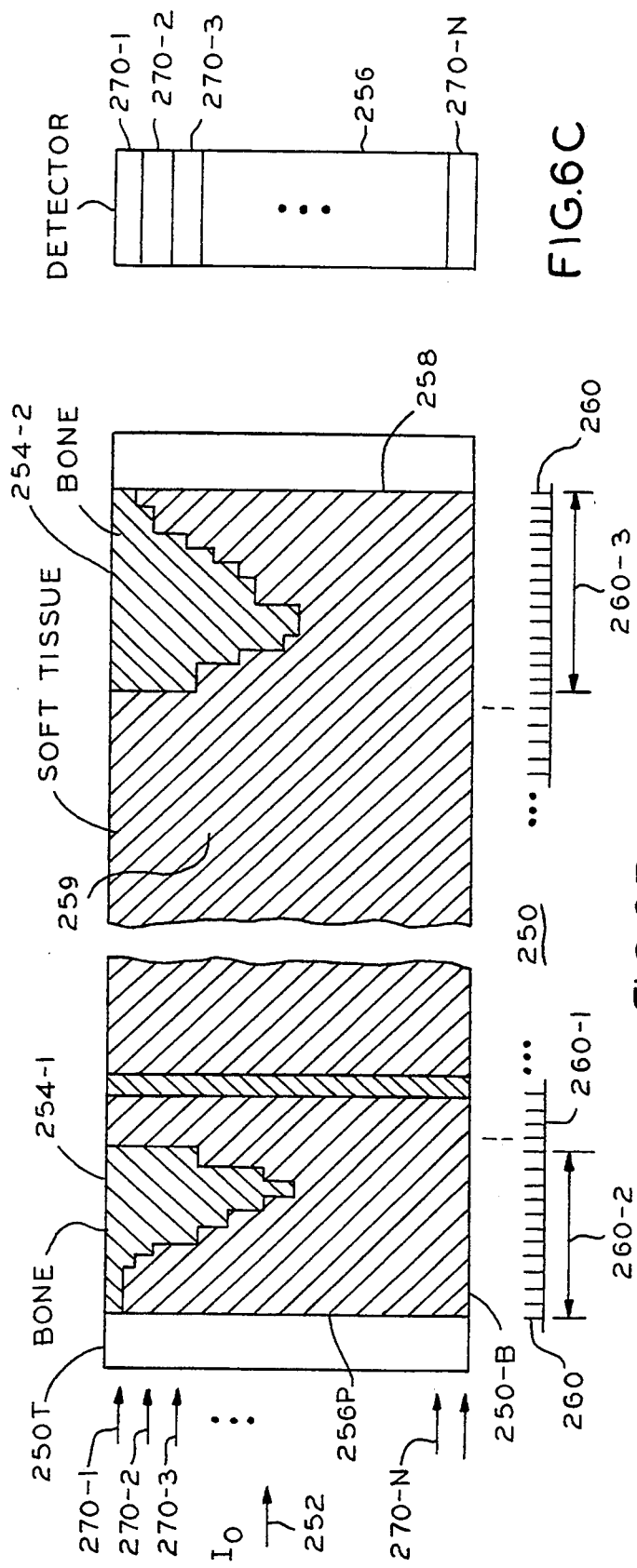
FIG.6A  FIG.6B  FIG.6C

REDUCED PARTIAL VOLUME ARTIFACTS IN IMAGE RECONSTRUCTION, WITH APPLICATION TO X-RAY COMPUTED TOMOGRAPHY

FIELD OF THE INVENTION

This invention relates to presentation of images of the type obtained by X-ray computed tomography, and more particularly to a reduction of artifacts in image reconstruction.

BACKGROUND OF THE INVENTION

In X-ray computed tomography a "slice" of an object is presented as an image on an imaging device, where the imaging device may be a cathode ray tube, a television screen, a plotter, etc. The image is created by first measuring the X-ray transmission of the object using "pencil" X-ray beams along many substantially parallel paths, for example 256 parallel pencil paths. Secondly, the orientation of the parallel paths is rotated through a small angle and the transmission measurements are repeated. Typically, a set of parallel X-ray transmission measurements are made at every one degree of rotation for each of the 180 degrees of a half circle. In this example, there will be 256 parallel measurements of X-ray transmission for each of 180 degrees, to give a total of 46,080 transmission measurements. Thirdly, a computer then uses this large number of X-ray transmission measurements in order to compute the X-ray attenuation coefficients in each volume element of the slice. A volume element of the slice will hereinafter be referred to as "voxel". The values of the X-ray attenuation coefficients are then converted to a set of "gray scale" values, and the gray scale values are presented as the image on the imaging device.

The image presented on the imaging device, such as a television screen or a plotter, are presented as "pixels". The two dimensional image is made of rows and columns of pixels, each pixel is represented by a digital number, and the digital number controls the display presented in the pixel.

A pixel represents the image of a voxel. The voxel is the three dimensional box within the object to be imaged, such as a patient, and the voxel contains materials of the object. The contents of the voxel are computed by an image reconstruction calculation, and are obtained as a number representing the X-ray attenuation of the material contained within the voxel. The number is then used to control the display presented in the pixel.

Many variations in making the X-ray transmission measurements have been used. For example, fan beam geometries have been employed rather than parallel beam geometries. A fan beam is produced by having one X-ray tube, and having many pencil beams collimated from this X-ray tube. A separate detector is installed for each pencil beam of the fan beam. The X-ray tube, collimators, and detectors are all mounted on a rotatable gantry so that the assembly may be rotated relative to the object, such as a patient. In a fan beam, the X-ray pencil beams make a small angle to each other, rather than follow parallel paths. The fan beam is used for transmission measurements at one orientation, and then the entire fan beam is rotated relative to the object, and in the plane of the desired slice, in order to produce another set of X-ray transmission measurements. The image of the slice is then reconstructed from the set of fan beam measurements made at each of the rotation angles.

The pencil X-ray beams naturally diverge, rather than maintain a parallel pencil structure. Divergence of the individual pencil beams may be accounted for in the image reconstruction process. For example, transmission measurements may be made at each angle through a rotation of 360 degrees, and oppositely directed measurements may be averaged together in order to account for divergence of the pencil beams.

Further, the object may be moved along the axis of the gantry in order to rapidly obtain transmission measurements for several parallel slices. Continuous motion of the object along the axis of the gantry causes the transmission measurements to produce a spiral pattern within the object, but still the X-ray transmission coefficient of a voxel may be computed by the computer.

Various difficulties arise in the computation of the X-ray transmission coefficient for a voxel. One difficulty arises from the fact that the X-ray attenuation coefficient of a material depends upon the atomic number of each element comprising the material, and also upon the density of the material. For example, water is made of hydrogen and oxygen, and tissue is made of hydrocarbon molecules which are principally made of hydrogen, carbon, and oxygen. In contrast, bone has a large component of calcium. Bone, accordingly, is made of materials having higher atomic number than soft tissue or water. Further, bone is considerably more dense than soft tissue or water. Accordingly, bone has a significantly higher attenuation coefficient for X-ray photons ordinarily used in X-ray tomography.

A difficulty in reconstructing the image from the X-ray transmission measurements arises in imaging a slice of a patient, where the slice contains both bone and soft tissue. It is usually desired to reconstruct an image of the soft tissue. For example, when it is desired to image a patient's brain, a slice of the patient's head is imaged. The head consists of a skull made of dense bone containing calcium, and a brain made of soft tissue composed of mainly water and hydrocarbons. Accordingly, the dense, calcium containing, skull has a significantly higher X-ray attenuation coefficient than does the soft tissue brain.

An artifact is introduced into the computation of the X-ray attenuation coefficient of each voxel by the "partial volume" effect. The partial volume effect is the effect on image reconstruction produced by a voxel containing two different materials, where the two different materials have different X-ray attenuation coefficients. For example, in imaging a patient's head, a voxel may contain both skull and soft tissue. A voxel near the brain-skull interface will contain both skull and soft tissue.

In imaging a patient's brain, a transmission measurement will contain bone at both the point where the X-ray beam enters the head, and also where the X-ray beam exits the head. As a result, the reconstructed X-ray density along the line of the X-ray beam may be erroneously high, leading to a streak in the image. This streak effect is particularly troublesome in image regions where the amount of bone in neighbor voxels changes along the line of the X-ray pencil beam. For example, curvature of the skull in a plane perpendicular to the plane of the slice may cause varying amounts of bone to project into voxels lying along a line of an X-ray pencil beam.

A particularly disadvantageous result of the partial volume effect is that the reconstructed image contains streak artifacts. Further, the value of X-ray attenuation coefficient computed in a voxel will depend upon a number of extraneous factors such as the partial volumes of neighbor voxels. For example, in imaging a patient's head, a number of the X-ray pencil beams may be substantially tangent to the interface between the skull and the brain, resulting in a line of voxels having rather large partial volume effects. Further, an X-ray pencil beam perpendicular to the skull and passing through the same voxel as the tangent pencil beam will have only a few voxels exhibiting a partial volume effect. The ordinary computational procedure for reconstructing the image cannot properly handle this variety of partial volume effects.

Previous methods of correcting a CT image for volume average effects have included simply lumping the run length of volume averaged voxels together into a combined voxel, and computing a correction X-ray attenuation coefficient for the combined voxel. The paper by D. J. Goodenough, K. E. Weaver, H. Costaridou, H. Erdmans, and P. Huysmans, "A New Software Correction Approach to Volume Averaging Artifacts in CT", published in "Computerized Radiology", Vol. 10, Nos. 2/3, Pages 87–98, 1986, discloses combining the voxels of the run length of volume averaged voxels into an effective voxel.

A further previous method looks at the slice above and the slice below the slice of interest, and establishes an order for three sublayers in the slice of interest in accordance with the values of X-ray attenuation coefficient calculated in the upper slice and the lower slice during the original reconstruction of the image. Values of X-ray attenuation coefficient are then assigned to the three sublayers in the slice of interest by interpolating the values of X-ray attenuation coefficient given for the slice above and the slice below. This method is disclosed in the paper by G. H. Glover and N. J. Pelc, "Nonlinear Partial Volume Artifacts in X-ray Computed Tomography", "Medical Physics", 7(3), pages 238–248 (May/June 1980).

There is needed a method to reconstruct an image from X-ray transmission measurements which will reduce artifacts arising from an interface in the object being imaged, where the interface is formed by two materials having different X-ray absorption characteristics. In particular, there is needed a method for reconstructing images having an interface between bone and soft tissue.

SUMMARY OF THE INVENTION

An image produced by a computed tomography reconstruction an object having volume averaged voxels has a calculation of a correction image, and an addition of the correction image to the original reconstructed image.

An apparatus for correcting an X-ray tomographic image is presented, where the tomographic image is created by measuring an X-ray transmission coefficient at each of a plurality of X-ray beam paths through an object to enable reconstructing a tomographic image of the object.

There is a means for selecting a plurality of volume averaged voxels along at least one of the X-ray beam ray paths, and for placing contiguous volume averaged voxels in a run length of volume averaged voxels, to make a plurality of run lengths of volume averaged voxels. There is a means for dividing the plurality of run lengths of volume averaged voxels into a plurality of subslices. There is a means, responsive to the plurality of subslices and responsive to the plurality of run lengths of volume averaged voxels, for computing a corrected value of X-ray attenuation coefficient for the X-ray beam ray path. There is a means for reconstructing a correction image using the corrected X-ray attenuation coefficient for each X-ray beam ray path. Finally, there is a means for obtaining an improved image by combining the tomographic image with the correction image.

Further, there is a means for determining an X-ray attenuation coefficient in a voxel in an upper slice above the slice of interest, and for determining an X-ray attenuation coefficient in a voxel in a lower slice below the slice of interest, and there is a means, responsive to determining the X-ray attenuation coefficient in the upper slice and responsive to determining the X-ray attenuation coefficient in the lower slice, for ordering the subslices so that an upper subslice corresponds to a material in a voxel in said upper slice. Each of the subslice may have the same thickness.

In an alternative embodiment of the invention, a thickness of each subslice is determined by a value of protrusion of a first material from above, where that value of thickness is computed for each run length of voxels.

A correction image is computed. The correction image is added to the original tomographic image to give an improved image.

BRIEF DESCRIPTION OF THE DRAWINGS

FIG. 1 is a side cutaway view showing an X-ray beam penetrating a patient's head.

FIG. 2 is a perspective figure showing two slices of reconstructed images.

FIG. 3 is a perspective, cutaway, view showing two slices of reconstructed images.

FIG. 6A is a graph illustrating CT Numbers obtained from a head scan.

FIG. 6B is a cross sectional drawing showing one X-ray beam path in a head scan.

FIG. 6C shows a detector in relation to the cross section of FIG. 6B.

is a side view showing a run length of voxels.

Figure 7A:
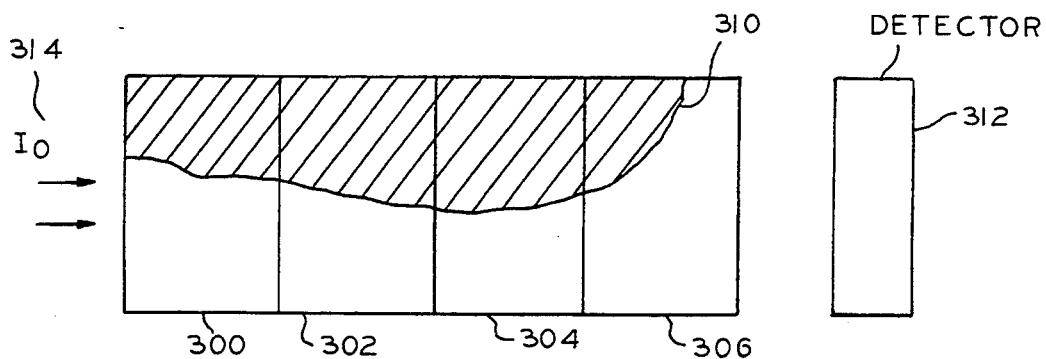
Figure 7B:
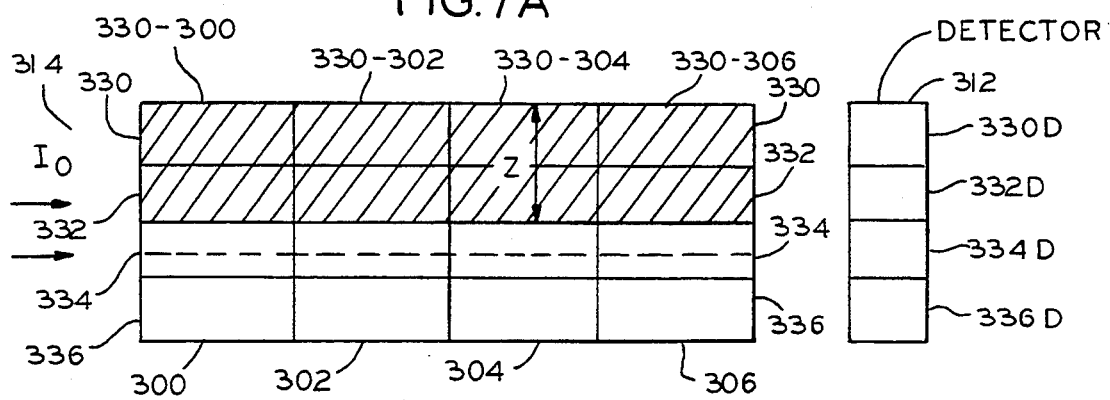
Figure 7C:
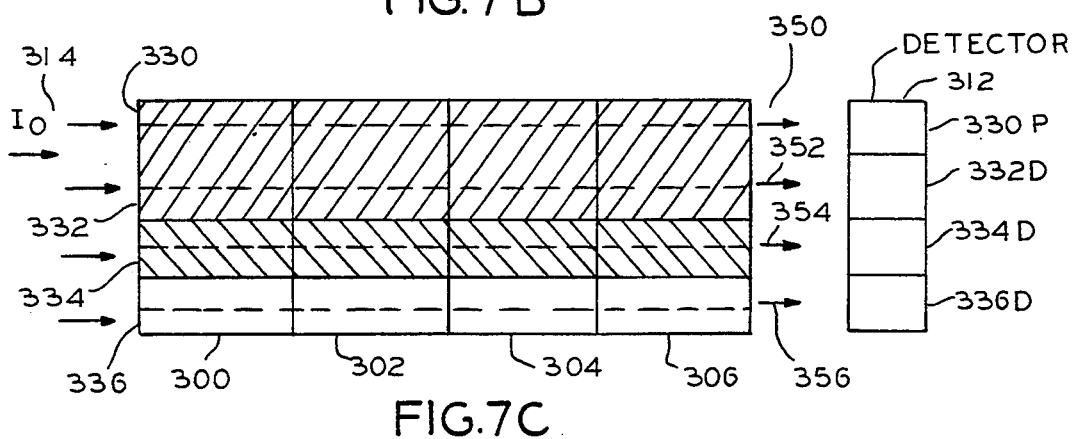

FIGS. 7A, 7B, 7C are side views of a run length of voxels in accordance with the invention.

Figure 7D:
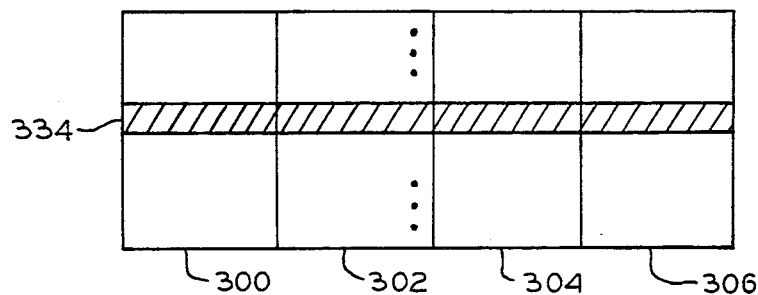

FIG. 7D is a correction subslice in accordance with the invention.

FIGS. 8A, 8B, 8C, 8D are a flow chart illustrating the invention.

Figure 9A:
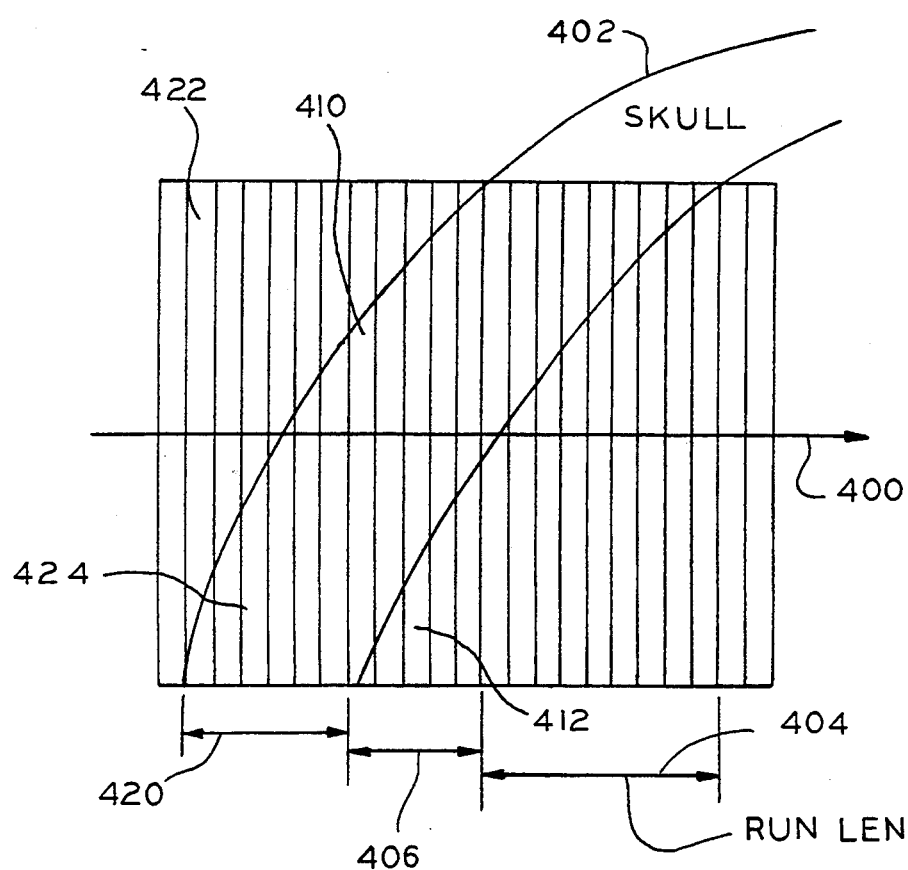
Figure 9B:
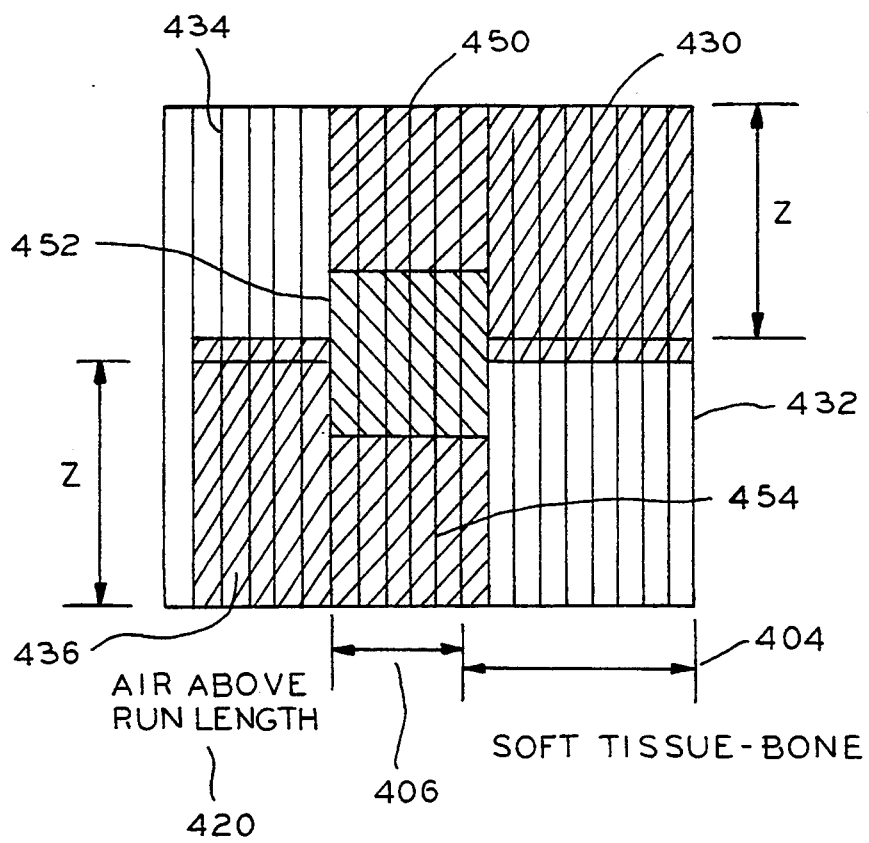

FIGS. 9A, 9B show voxels along a beam path, and in a plurality contiguous run lengths.

Figure 10A:
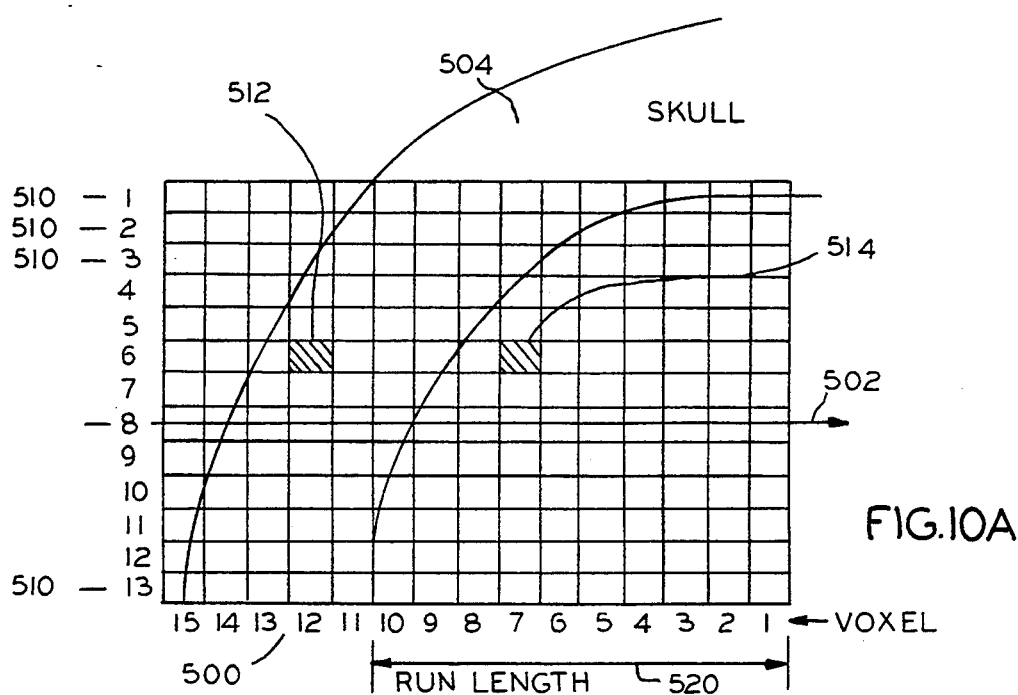
Figure 10B:
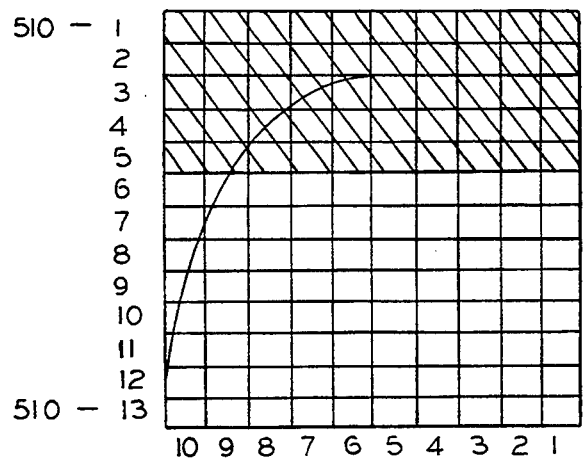
Figure 10C:
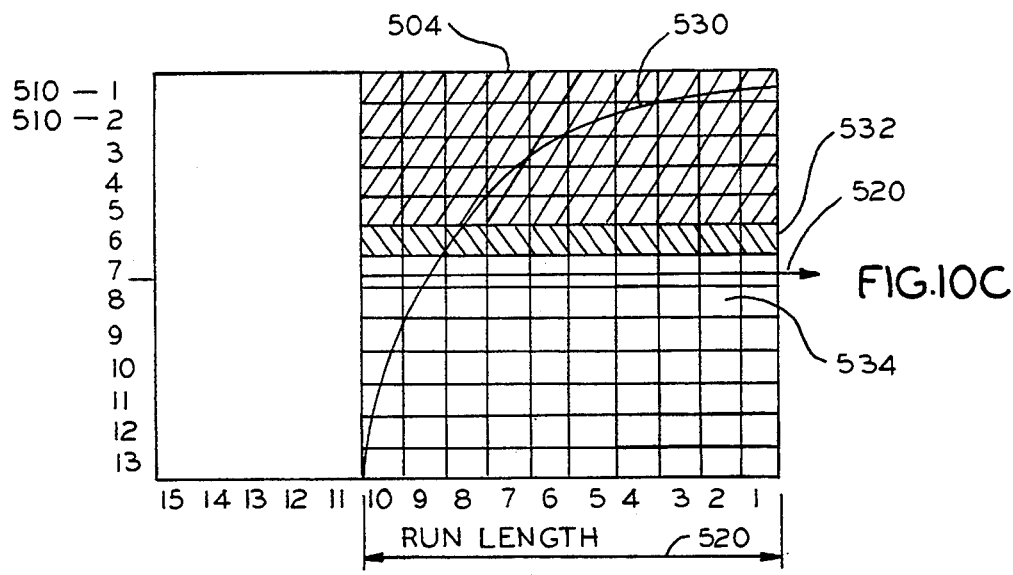

FIGS. 10A, 10B, 10C show voxels in a run length.

Figure 11A:
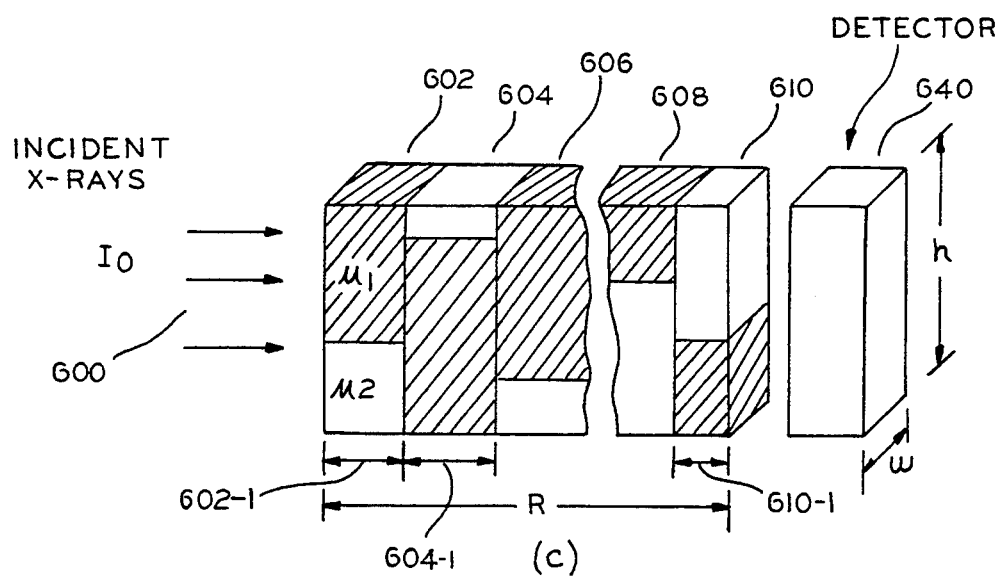
Figure 11B:
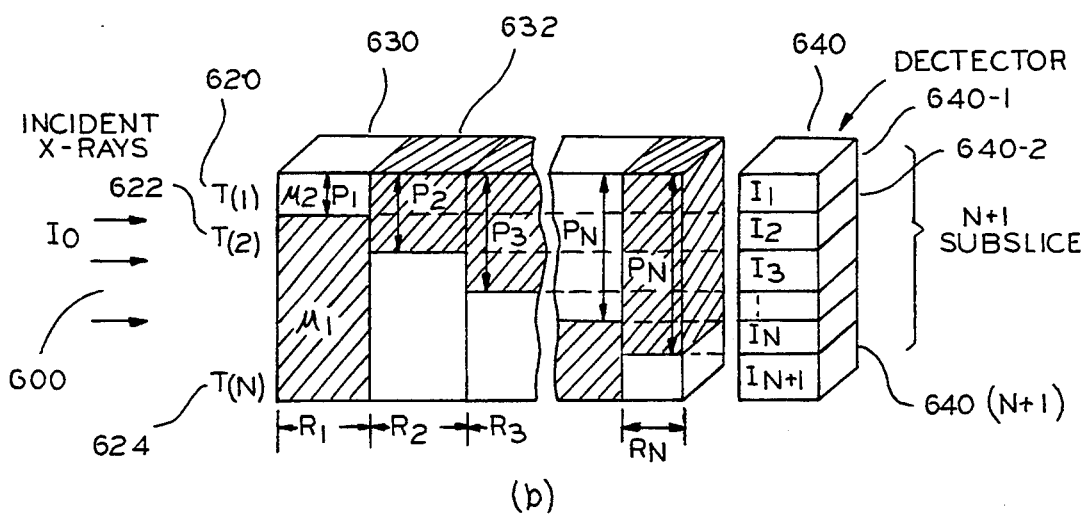

FIG. 11A is a perspective drawing of a plurality of run lengths of volume averaged voxels. FIG. 11B shows the run lengths of FIG. 11B after re-arrangement.

Figure 12:
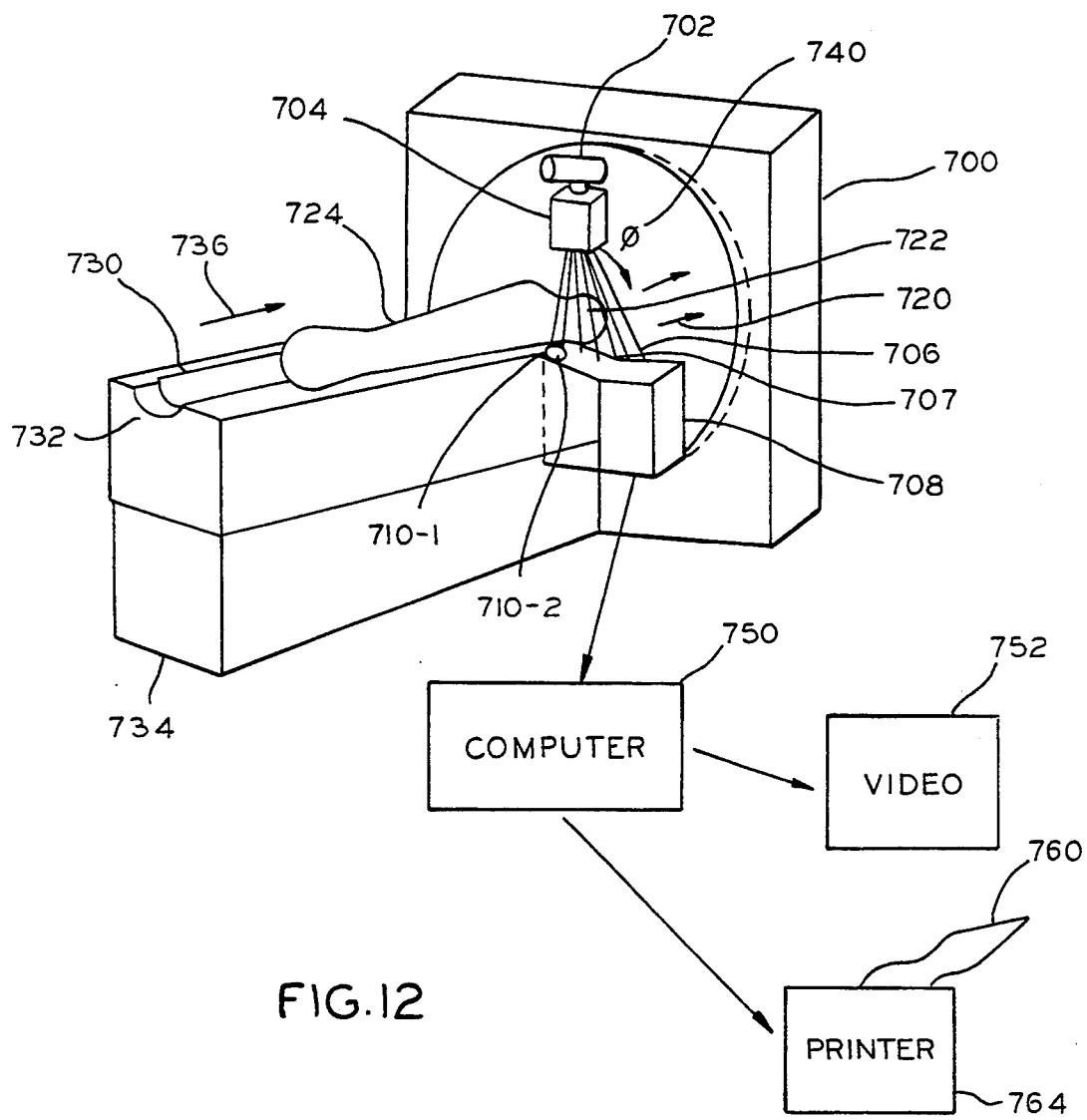

FIG. 12 is a perspective, and schematic, drawing of an X-ray computed tomography apparatus.

Figure 13:
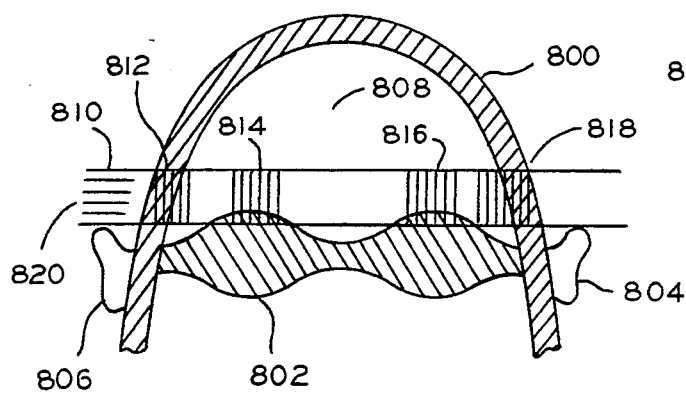

FIG. 13 is a cross section of a skull.

FIG. 14A, 14B, 14C, and 14D show X-ray tomography of an industrial object such as a ship propeller.

DETAILED DESCRIPTION

There is shown in FIG. 1 an X-ray pencil beam 100 produced by X-ray tube 102 and detected by X-ray detector 104. X-ray pencil beam 100 is shown entering a patient's head 106 at point 108 and exiting the patient's head 106 at point 110. X-ray pencil beam 100 has sides 120, 122. FIG. 1 shows that sides 120, 122 of X-ray pencil beam 100 diverge slightly. Ideally, sides 120, 122 would be parallel to form a parallel pencil beam. However, an X-ray beam is formed by collimation, and so the sides 120, 122 always diverge slightly. The slight divergence of the X-ray beam in modern tomographic scanners is small enough that it does not play a significant role in the present invention.

Turning now to FIG. 2, there is shown two slices 140, 142 of reconstructed images from an X-ray computed tomographic scan (often referred to as a CT scan) of a patient's head 106. Slice 140 is at a level of the patient's eyes. Slice 142 is at a level near the apex of the skull. Slice 140 has axial thickness 144. Slice 142 has axial thickness 146.

The image of each slice 140, 142 is reconstructed using a standard reconstruction computational procedure. A back-projection algorithm is typically used for the image reconstruction. A brief description of a typical reconstruction computational procedure is given in Appendix A. A reconstructed image is formed from values of X-ray attenuation coefficient calculated for each voxel. If $\mu(i,j)$ represents the X-ray attenuation coefficient calculated for a particular voxel designated by the indexes i and j in a particular slice, then a CT value is assigned to that voxel in accordance with the equation:

$$CT(i,j) = K \, (\mu(i,j) - \mu(\text{water}))/\mu(\text{water}) \quad \text{Equation EQ 1}$$

That is, the fractional difference between the X-ray attenuation coefficient computed by the reconstruction calculation, and the X-ray attenuation coefficient of water, is computed. This fractional value is multiplied by K, where K may be typically a number such as 500 or 1000, to give the CT value for the voxel. The CT values for the voxels of a slice are then converted to a scale of gray and presented on an imaging device such as a television screen.

Accordingly, water has a CT value of 0, and typically, K is chosen so that soft tissue has CT values in the range of approximately 0 to 100, bone has CT values in the range of approximately 800 to greater than 1000, and air has a negative CT value where the value is approximately −1000.

The difference between the reconstructed value of X-ray attenuation coefficient $\mu(i,j)$ and the X-ray attenuation coefficient for water is used to create the scale of gray image because soft tissue, the subject of most imaging procedures, has an X-ray attenuation coefficient near to that of water. Thus by subtracting the X-ray attenuation coefficient of water, the image enhances the difference between soft tissue and water, and thus, hopefully enhances the appearance of lesions having X-ray attenuation coefficients slightly different from either soft tissue or water.

Turning now to FIG. 3, the volume average effect is illustrated. Slice 140 having thickness 144 is shown intercepting two low density pathological areas 150, 152 of the patient's brain 154. Enlargement 156 shows how the pathological area 150 is distributed into two voxels 160, 162. Brain tissue 164A, 164B has a greater X-ray density than does pathological area 150A, 150B. In voxel 156, pathological area 150A is at the lower side of the voxel 156, while the higher X-ray density brain tissue is in the upper half of the voxel 156. The standard reconstruction algorithm which computes the image data in slice 140 will simply compute an "average" X-ray density for voxel 156, as well as for any voxel containing a plurality of materials where each material has a different X-ray density.

Enlargement 170 illustrates the situation where dense bone 172 is shown occupying the upper portion of voxel 174. Lower X-ray density brain material 176 occupies a lower portion of voxel 172. Again, the standard reconstruction computational procedure is intended to give some form of "average" value for the X-ray attenuation of voxel 172.

Similarly, voxel 180 has an upper side occupied by dense bone material 182, and a lower portion occupied by less dense brain material. Again, the standard image reconstruction computational procedure will simply give some form of "average" values of computed X-ray attenuation in each of the voxels occupied by more than one material. Even more serious, the standard image reconstruction computational procedure will produce "streak" artifacts in a situation such as slice 142 where voxel 172, 180 are on one side of an image, and there are corresponding voxels 190, 192 on the other side of the image. The voxels having partial occupancy by dense bone cause errors in the reconstructed image along a line joining the regions. These reconstruction errors cause streaks to appear in the image, and are referred to as streak artifacts.

Figure 4:
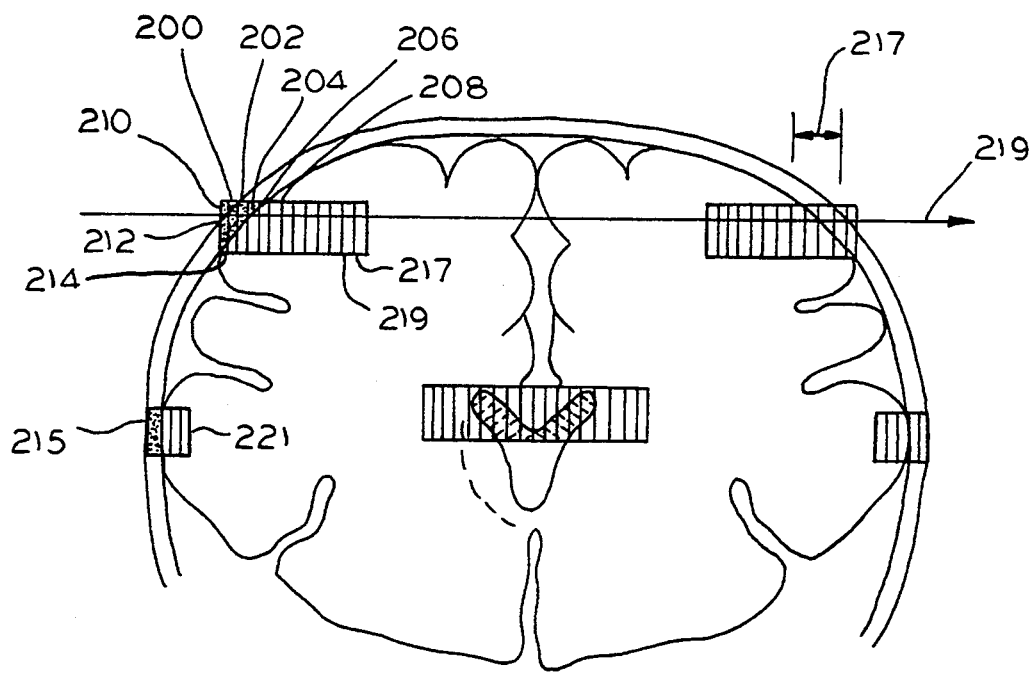
FIG. 4 is a top, cutaway, view showing voxels in relationship to a patient's skull.

Turning now to FIG. 4, there is shown a line of voxels 200, 202, 204, 206, 208 having different partial occupancy by dense bone of skull 210. Voxel 200 has air in region 210, has dense bone in region 212, and has brain tissue or water in region 214. Similarly, voxel 202 contains three regions of different X-ray attenuation, air, bone, and brain tissue. In contrast, voxel 208 and voxel 210 contain only bone to the left and brain tissue to the right, as shown in FIG. 4.

A second run length 217 lies along X-ray beam ray path 219.

Figure 5:
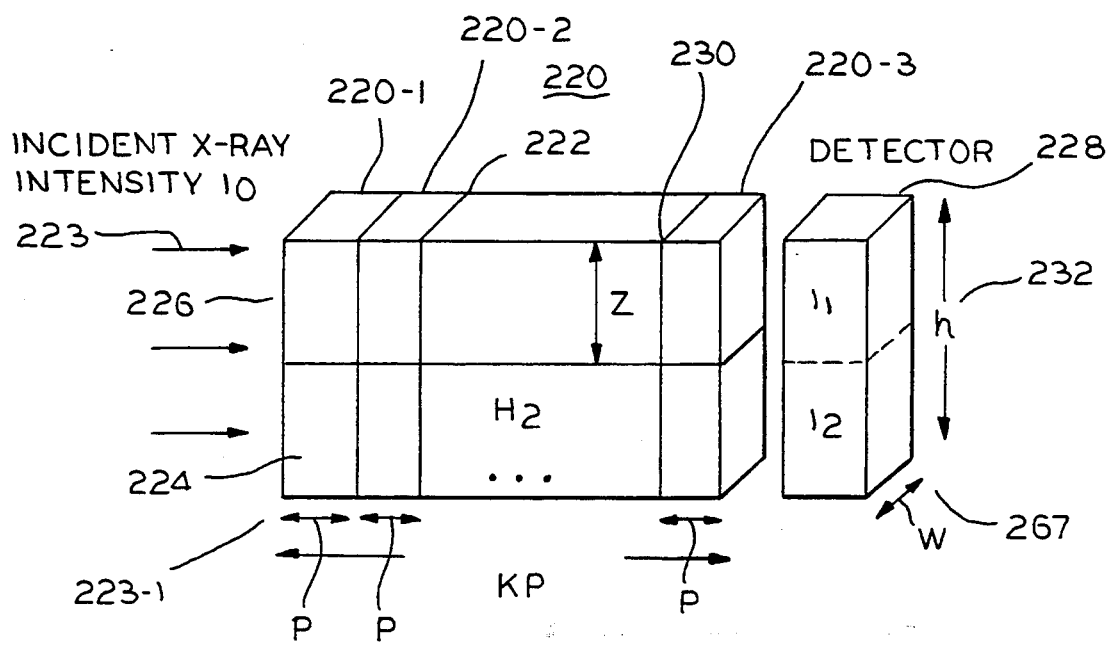
FIG. 5 is a perspective view showing a run length of voxels and an X-ray detector.

Turning now to FIG. 5, there is illustrated generally a run length of contiguous voxels 220. The run length of contiguous voxels 220, has voxels 220-1, 220-2, . . . 220-3. Each voxel has length p 223-1 in the direction of the X-ray beam, illustrated by arrows 223. There are K voxels in the run length. Voxels 220-1, 220-2, . . . 220-3 are occupied by two materials of different X-ray attenuation. A first material 222 has an X-ray attenuation coefficient $\mu(1)$. A second material 224 has an X-ray attenuation coefficient $\mu(2)$. The incident X-ray intensity on the left at location 226 is I(0). The intensity incident on detector 228 is I(1) for the part of the X-ray beam passing through material 222, and is I(2) for the part of the X-ray beam passing through material 224. The total intensity detected by detector 228 is I(1)+I(2).

The thickness of the run length of voxels 220 is given by $$R = K \, p$$

The effective X-ray attenuation coefficient for voxels 222 is given by solving the following equation for $$I(1) + I(2) = I(0) \exp(-\mu(\text{eff}) R).\qquad \text{Equation EQ 2}$$

This equation permits $\mu(\text{eff})$ to be written in terms of $\mu(1)$ and $\mu(2)$, Z 230 the thickness of material 222, and h 232 the thickness of the voxel:

$$(Z/h) \exp(-\mu(1) R) + \qquad \text{Equation EQ 3}$$
$$((Z - h)/h) \exp(-\mu(2) R) = \exp(\mu(\text{eff}) R)$$

Solving this equation for $\mu(\text{eff})$ gives:

$$\text{Equation EQ 4}$$
$$\mu(\text{eff}) = \mu(2) - (1/R) \text{Ln}(1 + (z/h) \exp((\mu(2) - \mu(1)) R) - 1)$$

where Ln stands for the logarithm to base e.

The ordinary image reconstruction, such as a filtered back projection etc., simply calculates a $\mu(\text{calculated})$ for each voxel. This $\mu(\text{calculated})$ is generally different for each voxel. However, the value of $\mu(\text{calculated})$ does not give the fractional composition Z/h of $\mu(1)$ material and the fractional composition $(1-Z/h)$ of $\mu(2)$ material.

A correction to the ordinary image reconstruction computation is based, in part, on the above equation for $\mu(\text{eff})$.

Turning now to FIG. 6B there is shown a cross section of a patient's head. The cross section is shown generally as cross section 250. X-ray beam path 252 penetrates the cross section 250, and the intensity emerging from the cross section is detected by detector 256 of FIG. 6C. Bone 254-1, 254-2 is shown growing into the slice from the top. Cross section 250 represents one row of voxels in a reconstruction slice, such as the slices 144, 146 shown in FIG. 2. The height 144, 146, shown in FIG. 2, of a slice is given by height 250-B to 250-T, where B stands for bottom and T stands for top. The x-ray beam enters the patient's head along direction 252, at point 256, exits the cross section of the patient's head at point 258, and is detected by detector 256.

Voxels used for the original image reconstruction are shown by marks 260. Voxel 260-1 is completely filled by soft tissue 259. Voxels indicated by line 260-2 are volume averaged since they are partially occupied by bone 254-1, and partially occupied by soft tissue 259. Voxels 260-3 are also volume averaged because they are partially occupied by bone 254-2 and by soft tissue 259.

In FIG. 6A there is shown a graph of CT counts obtained by the original image reconstruction. The original image reconstruction was done using thousands of measurements of X-ray beam penetration along different X-ray beam paths 252, and then calculating an image reconstruction as described in Appendix A. The CT numbers shown in FIG. 6A give air as approximately $-1000$, water as zero, 0, soft tissue as approximately 100 to 200, and bone as approximately $+1000$. These values of CT numbers are based upon water and soft tissue having an X-ray attenuation of 0.2 cm$(-1)$, to one decimal point, and bone having an X-ray attenuation of approximately 0.4 cm$(-1)$.

In accordance with the invention, the slice 144, 166 of cross section 250 is divided into subslices 270-1, 270-2, 270-3, ... 270-N. Also, detector 256 is divided to correspond to subslices 270-1, 270-2, ... 270-N, as shown in FIG. 6C. A correction to the original image reconstruction is computed on the basis of subslices 270-1, 270-2, ... 270-N.

Voxels 260-2 represent a run length of volume averaged voxels. Voxels 260-3 represent another run length of volume averaged voxels. Both run lengths, of voxels 260-2 and voxels 260-3 lie along the same X-ray beam path 252. Calculation of the correction to the original reconstructed image is discussed further hereinbelow.

First Exemplary Embodiment of the invention

In an exemplary embodiment of the invention, a correction image is computed as follows. The correction image is then added to the original reconstructed image, to form an output image. Increased accuracy of fractional composition of $\mu(1)$ material and $\mu(2)$ material is obtained, and artifacts in the reconstructed image are reduced from those present in the original reconstructed image.

The first step in obtaining the correction image is to choose an X-ray beam ray path, and to search, along the ray path, through the voxels looking for voxels which apparently have volume averaged values.

It is expected that X-ray attenuation coefficients have fairly standard values for an X-ray tube operating at a given voltage. For example, for an X-ray tube operating at 120 thousand volts the value of $\mu$ for air is essentially zero, for water or soft tissue is about 0.19 to 0.20 cm$(-1)$. For bone the value of $\mu$ has a fairly wide range, depending upon the biological properties of a particular bone, One approach is to use the largest voxel value of $\mu$ computed in a slice as the $\mu$ of bone, on the grounds that this voxel probably had very little volume averaging.

In searching along an X-ray path, voxels having a computed value of X-ray attenuation coefficient $\mu$ near that expected for water or soft tissue are assumed to not be volume averaged, and also those voxels having the computed X-ray attenuation value selected as the value of bone are assumed not to be volume averaged. Referring to FIG. 4, voxel 215 would be taken as having the X-ray attenuation coefficient of bone, while voxels 217, 219, 221 would be taken to be fully occupied by soft tissue.

Voxels having computed X-ray attenuation coefficient values between the value for soft tissue and for bone are assumed to be volume averaged. For example, in FIG. 4, voxels 200, 202, 204 and 206 will have computed $\mu$ values between those for soft tissue and for bone. Accordingly, voxels 200, 202, 204 and 206 will be selected as being volume averaged.

Accordingly, a sequence of contiguous voxels along a ray path, such as voxels 202, 204, and 206 are selected as a "run length" of volume averaged voxels. Voxel 200 is not chosen to be in the run length because voxel 200 contains too much air, and therefore contains three substances, air, tissue, bone, and the present focus is on voxels containing two substances.

The second step in computing the correction image is to analyze a run length of voxels in accordance with the model outlined herein above with reference to FIG. 5.

The average value of the X-ray attenuation coefficient for the run length of voxels is computed by adding the calculated value for each voxel and dividing by the number of voxels, and is referred to as $\mu(\text{av})$.

The value of Z/h for the run length of voxels is calculated from the formula:

$$\text{Equation EQ 5}$$
$$Z/h = (\exp(\mu(2) - \mu(\text{av})) R - 1)/(\exp(\mu(2) - \mu(1)) R - 1)$$

In equation EQ 5, R is the length of the run length of voxels. In the event that each voxel has the same dimension p along the X-ray beam path, and in the event that there are K voxels in the run length, then R is the value of p times K.

The third step in correcting the image is to determine whether the material having X-ray attenuation coefficient $\mu(1)$ or the material having $\mu(2)$ should be placed at the top or the bottom of the run length 250 of voxels. This decision is made by examining both the slice above and the slice below the slice of interest. For example, the X-ray attenuation coefficient $\mu(1)$ may refer to the larger value representative of bone. Then, if the slice above the slice of interest has voxels having higher values of $\mu(i,j)$ from the original reconstructed image, the larger values of $\mu(1)$ will be placed at the top of the voxels of run length 250 of volume averaged voxels.

The fourth step in correcting an image for volume averaged voxels is illustrated in FIGS. 7A, 7B, 7C, 7D.

In FIG. 7A a run length of voxels 300, 302, 304, 306 selected as having a CT number between that of bone and soft tissue is shown. For example, voxels 300, 302, 304, 306 may have been selected as having CT numbers between 300 and 700, where soft tissue is expected to have a value less than 100 and bone is expected to have a value above 800. The actual bone projection into the voxels 300, 302, 304, 306 is illustrated by wavy line 310 and the cross hatching. The cross hatched region is the actual bone projection of the patient, where the bone of the patient is superimposed on the voxels 300, 302, 304, 306 of the image reconstruction. Detector 312 detects the incident X-ray intensity I(0) 314 incident upon the ray path of the run length of voxels.

Turning now to FIG. 7B, the average value of the X-ray attenuation in voxels 300, 302, 304, 306 is calculated, and the average value shows that all voxels of subslices 330, 332 are to be modeled as bone, in accordance with the original image reconstruction. Modeling subslices 330, 332 as bone is indicated by cross hatching in these subslices.

Also illustrated in FIG. 7B are subslices 330, 332, 334, 336. Subslices 330, 332, 334, 336 are subdivisions of the run length of voxels, where the subdivisions are taken both parallel to the direction of the incident X-ray beam and also parallel to dimension W 267 shown in FIG. 5. The portion of a voxel in one subslice is referred to as a "subvoxel". Subvoxels are denoted by both a subslice and a voxel designation. Subvoxel 330-300 is the part of voxel 300 which is in subslice 330, subvoxel 330-302 is the subvoxel of voxel 302 which is in subslice 330, etc. Dimension W 267, shown in FIG. 5, is perpendicular to the plane of FIG. 7B, and so is not shown in FIG. 7B. Also, detector 312 is divided into subslices 330D, 332D, 334D, 336D. The portion of the X-ray incident intensity 314 which penetrates the voxels 300, 302, 304, 306 along subslice 330 is detected by the portion of detector 312 indicated by detector subslice 330D. Likewise, that portion of incident X-ray intensity 314 which penetrates the voxels along subslice 332 is detected by the part of detector 312 indicated by subslice 332D. Similarly for each subslice through the voxels, that portion of incident X-ray intensity 314 which penetrates the voxels along a subslice is detected by a portion of detector 312 which is aligned with the subslice. Detector 312 is not physically divided, the volume of detector 312 is simply regarded as volumes corresponding to the various subslices into which the voxels are divided.

The number of subslices modeled as filled with bone is calculated from the average value of X-ray attenuation, $\mu$(avg) of voxels 300, 302, 304, 306. It is assumed that subslices 330, 332 are found, from $\mu$(avg), to be modelled as filled with bone, and this assumption is shown by cross hatching of subslices 330, 332 in FIG. 7B. All voxels of a subslice are assigned the same arrangement of subvoxels, having either the $\mu$ value of bone or the $\mu$ value of soft tissue, as further illustrated by the cross hatching of FIG. 7B.

Also shown in FIG. 7B is the value of Z/h computed for the run length of volume averaged voxels. The value of Z/h computed for the run length of voxels 300, 302, 304, 306 is shown by line 338 and arrow 339. Equation EQ 5 is used to compute the value of Z/h.

Although the value of h is not needed to complete the correction calculation, the value of h is ordinarily known from the settings of the X-ray scanner. For example, h may typically have a value of 1.0 centimeter. A typical run length of voxels in a head scan of a patient, where the slice is taken near the apex of the skull, may have, for example, ten voxels which are determined to be volume averaged.

Turning now to FIG. 7C, based upon the Z/h calculation, each subvoxel of each voxel is assigned the X-ray attenuation coefficient $\mu$ of either bone or, soft tissue. Subslices 330, 332 remain assigned to bone, as indicated by the single cross hatching. However, since the value of Z/h penetrates nearly through subslice 334, subslice 334 is also assigned to bone. This re-assignment of subslice 334 to be occupied by bone is further indicated in FIG. 7C by, double cross hatching.

Turning now to FIG. 7D, a difference X-ray attenuation value $\Delta\mu$ is shown in subslice 334. The value of $\Delta\mu$ is given by the value of $\mu$(bone)$-\mu$(soft tissue). The value of $\Delta\mu$ gives the "error in assignment" to subslice 334 by the original image reconstruction.

As further illustrated in FIG. 7C, an X-ray path 350, 352, 354, 356 is traced through each subslice 330, 332, 334, 336, respectively. Detector portion 330D detects the X-ray beam traced along X-ray path 350 through subslice 330. Detector portion 332D detects the X-ray beam traced along X-ray path 352 through subslice 332. That is, an X-ray path is traced along each subslice, and the corresponding portion of detector 312 detects that X-ray beam.

The total X-ray intensity which would have been detected by detector 312 is next computed, in the event that the slice had been physically resolved into subslices 330, 332, 334, 336, and in the further event that the voxels had been physically resolved into subvoxels as shown in FIG. 7C where the subvoxels contain bone or soft tissue, and if the detector 312 had been physically resolved into subslices 330D, 332D, 334D, 336D. The total X-ray intensity which would have been detected by detector 312 is the sum of the intensities penetrating the voxels 300, 302, 304, 306 along each X-ray beam path 350, 352, 354, 356.

A correction to the X-ray absorption coefficient in each subvoxel is computed using both the $\mu(i,j)$ value computed for the voxel in the original image reconstruction, and the value of Z/h computed for that run length.

Steps in computing the correction are as follows.

In the general case, there are several run lengths of volume averaged voxels along the X-ray beam path. There will generally be different numbers of voxels in each run length of volume averaged voxels.

A subslice is defined as extending along the entire X-ray beam path, and so the subslice cuts each voxel in each run length of volume averaged voxels into subvoxels.

Let there be M run lengths of volume averaged voxels, and indicate each by m. Let K(m) indicate the number of voxels in any particular run length of volume averaged voxels. Let the length, in the direction of the X-ray beam path, of a run length of volume averaged voxels be d(m). Accordingly d(m)=K(m) p, where p is the length of one voxel. There are N subslices defined through the voxels and parallel to the direction of the X-ray beam, and individual subslices are indicated by n.

1. The average value of $\mu(i,j)$ of the voxels in a particular run length is computed and is denoted as $\mu(avg)$. Another index k is introduced to indicate the voxels of a particular run length, so that the voxels in the run length have the X-ray attenuation values of $\mu(k(i,j))$. The symbol k(i,j) means that the voxel k of the run length is from row i, column j of the originally reconstructed image. Here k runs over the range $1 \ldots K$, where there are K voxels in the particular run length. The value of $\mu(avg)$ for a particular run length is then given as:

$$\mu(avg) = (1/K) \sum_{k=1}^{K} \mu(k(i,j)) \qquad \text{Equation EQ 6}$$

2. This value of $\mu(avg)$ is then used to calculate the number of subslices in a run length to be filled with high X-ray attenuation materials. First, it is determined, by examining slices above and below the slice of the X-ray beam path being presently considered, whether or not the high X-ray attenuation material enters the voxels from above or from below. In the example where the high X-ray attenuation material enters the voxels from above (below), the upper (lower) subslices are filled with the high $\mu$ material. High X-ray attenuation material has attenuation of $\mu(1)$, and low X-ray attenuation material has attenuation of $\mu(2)$. There are N(high) subslices with high X-ray attenuation material, and N(low) subslices with low X-ray attenuation material, and a total of N subslices.

$$N = N(high) + N(low) \qquad \text{Equation EQ 7}$$

Using this subslice model of the material, the average value X-ray attenuation of the run length is given as:

$$\mu(avg\ model) = (N(high)\ \mu(1) + N(low)\ \mu(2))/N \qquad \text{Equation EQ 8}$$

The number of subslices filled with high X-ray attenuation material can then be calculated by equating the average $\mu(avg)$ computed from the reconstructed image with the average given by the subslice model, as:

$$\mu(avg) = \mu(avg\ model) \qquad \text{Equation EQ 9}$$

Accordingly, the number of subslices filled with high X-ray attenuation material, on the basis of the original reconstructed image, and the model is given by:

$$N(high) = N\ (\mu(avg) - \mu(2))/(\mu(1) - \mu(2)) \qquad \text{Equation EQ 10}$$

3. The value of Z/h is used to calculate the number of subslices which should be filled by the high X-ray attenuation material, and this number of subslices is normally different from the number given by the simple average of the reconstructed X-ray attenuation values computed as N(high) hereinabove. The number of subslices filled with high X-ray attenuation material calculated from the value of Z/h is represented by the symbol N(high, Z/h) in order to distinguish it from the number given by the average of the original image reconstruction $\mu$ values. The value of N(high, Z/h) is given by:

$$N(high,\ Z/h) = N\ (Z/h) \qquad \text{Equation EQ 11}$$

3. A corrected number of subslices containing high X-ray attenuation material is then computed, and is represented as $\Delta N$, and the value of $\Delta N$ is given by:

$$\Delta N = N(high,\ Z/h) - N(high) \qquad \text{Equation EQ 12}$$

4. Assign additional (fewer) subslices to high X-ray attenuation material, where the additional (fewer) number of subslices so assigned is given by $\Delta N$. After this assignment, the model will have N(high, Z/h) subslices assigned to high X-ray attenuation material. In many image reconstruction techniques, such as are further discussed in the Appendix hereinbelow, the value of Z/h will require more subslices to be occupied with high X-ray attenuation material than is given by the average value $\mu(avg)$ obtained from the original image reconstruction.

5. A corrected value of X-ray attenuation is computed for the subslices reassigned to high X-ray attenuation material. The correction is represented by the symbol $\Delta\mu(n, m, k)$ for each subvoxel of the n subslice, of the m run length, of the k voxel. The value of n runs over subslices, from 1 to N. The value of m runs over run lengths from 1 to M. The value of k runs from 1 to K(m), where K(m) is the number of voxels in the m run length.

Additional indexes must be added to the X-ray attenuation coefficient $\mu$ in order to designate the method of computation, as well as the type of material and the subvoxel. Hereinabove, the symbol $\mu(1)$ designates high X-ray attenuation material, and the symbol $\mu(2)$ designates low X-ray attenuation material. The indexes "1" and "2" are kept to designate the materials. Accordingly, The symbol $\mu(2, n,m,k,$ original image reconstruction) represents the X-ray attenuation computed for subvoxel k, of the subslice n of the run length m, from the original image reconstruction, for subvoxels assigned to low X-ray attenuation material. The symbol $\mu(1, n,m,k, Z/h)$ represents the material of high X-ray attenuation computed for the subvoxel k, of the subslice n of the run length m, by the Z/h method. Accordingly, a subvoxel correction for subvoxels having their material reassigned from $\mu(1)$ to $\mu(2)$ as a result of the Z/h calculation is given by:

$$\Delta\mu(n,m,k) = \mu(1,\ n,m,k,\ Z/h) - \mu(2,\ n,m,k,\ \text{original image reconstruction}) \qquad \text{Equation EQ 13}$$

6. A corrected value of X,ray attenuation for the X-ray beam path is then calculated. The symbol $\mu(n,m,k)$ is introduced to represent the X-ray attenuation computed as a result of the correction in subslice n, in run length of volume averaged voxels m, in voxel k. The length of run length m is represented by d(m).

The intensity penetrating the run lengths of volume averaged voxels must also penetrate the voxels which were not selected as "volume averaged". However, each subslice is additionally attenuated by the voxels not selected as "volume averaged". Accordingly, attention is focused upon the total intensity penetrating the selected run lengths of volume averaged voxels.

The intensity penetrating one subslice n, through all run lengths of volume averaged voxels m, each containing K(m) voxels, is computed as follows:

INTENSITY (Penetrating Subslice n) =  Equation EQ 14

$(I(0)/N) \exp - (\mu(n,m = 1,1) d(m = 1) +$ $\mu(n,m = 1,2) d(m = 1) + \ldots + \mu(n,m = 2,1) d(m = 2) +$ $\mu(n,m = 2,2) d(m = 2) + \ldots + \mu(n,M,K) d(M))$ The total intensity penetrating all run lengths of volume averaged voxels is then computed by summing the intensities penetrating all run lengths of each subslice, and is given by:

TOTAL INTENSITY (all run lengths) =  Equation EQ 15

INTENSITY (Subslice 1) + INTENSITY (Subslice 2) +

$\ldots$ + INTENSITY (Subslice N)

Of course, the intensity penetrating the object being imaged is less than that computed from Equation EQ 15 because of the additional attenuation of the voxels which are not volume averaged. However, our attention is focused on only the effect of the volume averaged voxels.

Equation 15 may be written as a sum with n running over all subslices, m running over all run lengths of volume averaged voxels, and k running over all subvoxels of a subslice along the run length, as:

$$I\left(\frac{\text{total penetrating}}{\text{all volume averaged voxels}}\right) = \quad \text{Equation EQ 16}$$

$$I_0 \sum_{n=1}^{N} e - \left(\sum_{m=1}^{M} \sum_{k=1}^{K(m)} \mu(n,m,k) d(m)\right)$$

The total length of all run lengths is represented by the symbol d(total), m runs over all run lengths M, and d(total) is given by:

$$d(\text{total}) = \sum_{m=1}^{M} d(m) \quad \text{Equation EQ 17}$$

A corrected value of X-ray attenuation was computed hereinabove, for each subvoxel of each subslice, in each run length of volume averaged voxels, and was represented by the symbol, $\Delta\mu(n, m, k)$, and this symbol is used hereinbelow.

The expression for $\mu$(correction) may be written out as:

$d(\text{total}) \mu(\text{correction}) = \quad \text{Equation EQ 18}$

-continued $$\text{Ln}\left(\sum_{n=1}^{N} e - \left(\sum_{m=1}^{M} \sum_{k=1}^{K(m)} \Delta\mu(n,m,k) d(m)\right)\right)$$

Ln stands for the logarithm to base e. A value of $\mu$(correction) is computed for each beam ray path for which measurements were made in taking the original X-ray penetration measurements. For example, in the event that there were 180 angular measurements, and 256 parallel measurements made at each angle, then there will be 180*256=46,080 $\mu$(correction) values computed.

In the simple case where there is only one run length, the expression for $\mu$(correction) reduces to simply the sum of the $\Delta\mu$ values for the subvoxels of that single run length of volume averaged voxels.

Several different run lengths of volume averaged voxels may be discovered along any particular X-ray beam path, as shown in FIG. 6. The subslices are defined along the X-ray beam path, and so cut each of the run lengths, and so divide the voxels of each run length into subvoxels. The exact expression of Equation EQ 18 must then be used to calculate $\mu$(correction).

The fifth step in computing a correction image is to use the above computed values of $\mu$(correction) in order to reconstruct an image, called the correction image. For example, the correction image is computed using the same back projection computational method that the original image reconstruction used. The correction image will yield a correction value of X-ray attenuation coefficient for each voxel.

The sixth step in computing the correction image is to add the correction image to the original image, to produce the output image. The CT numbers of the output image are converted to a scale of gray image, and the scale of gray image is presented on an imaging device such as a television screen.

Figure 8A:
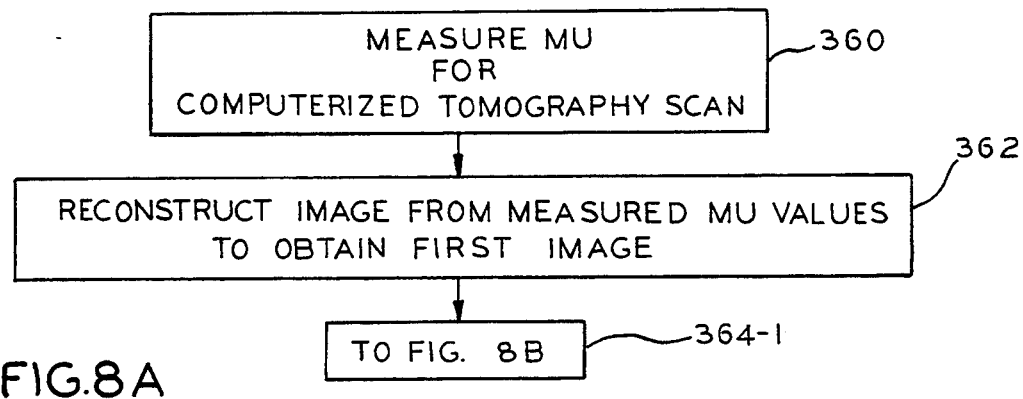
Figure 8B:
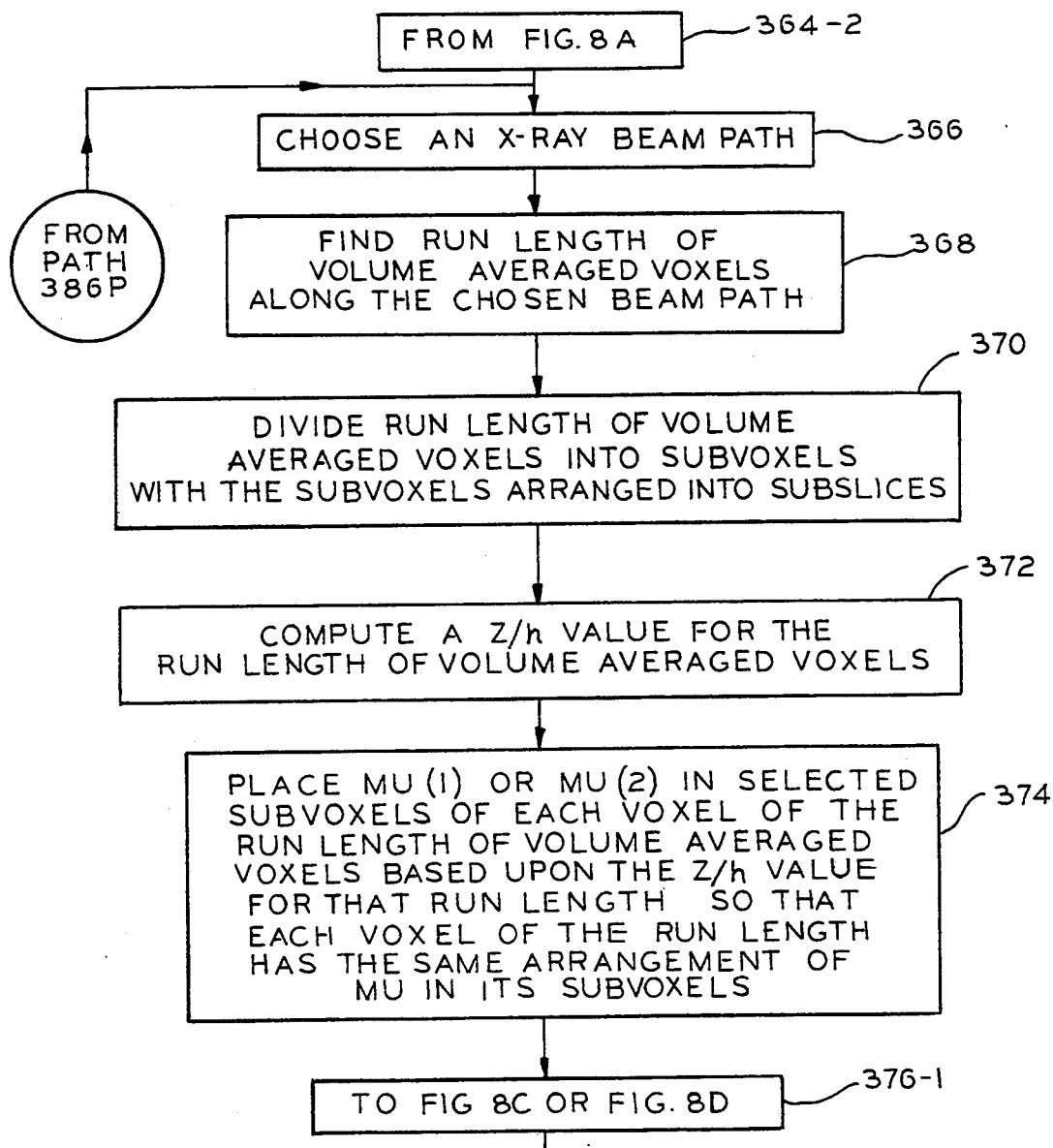
Figure 8C:
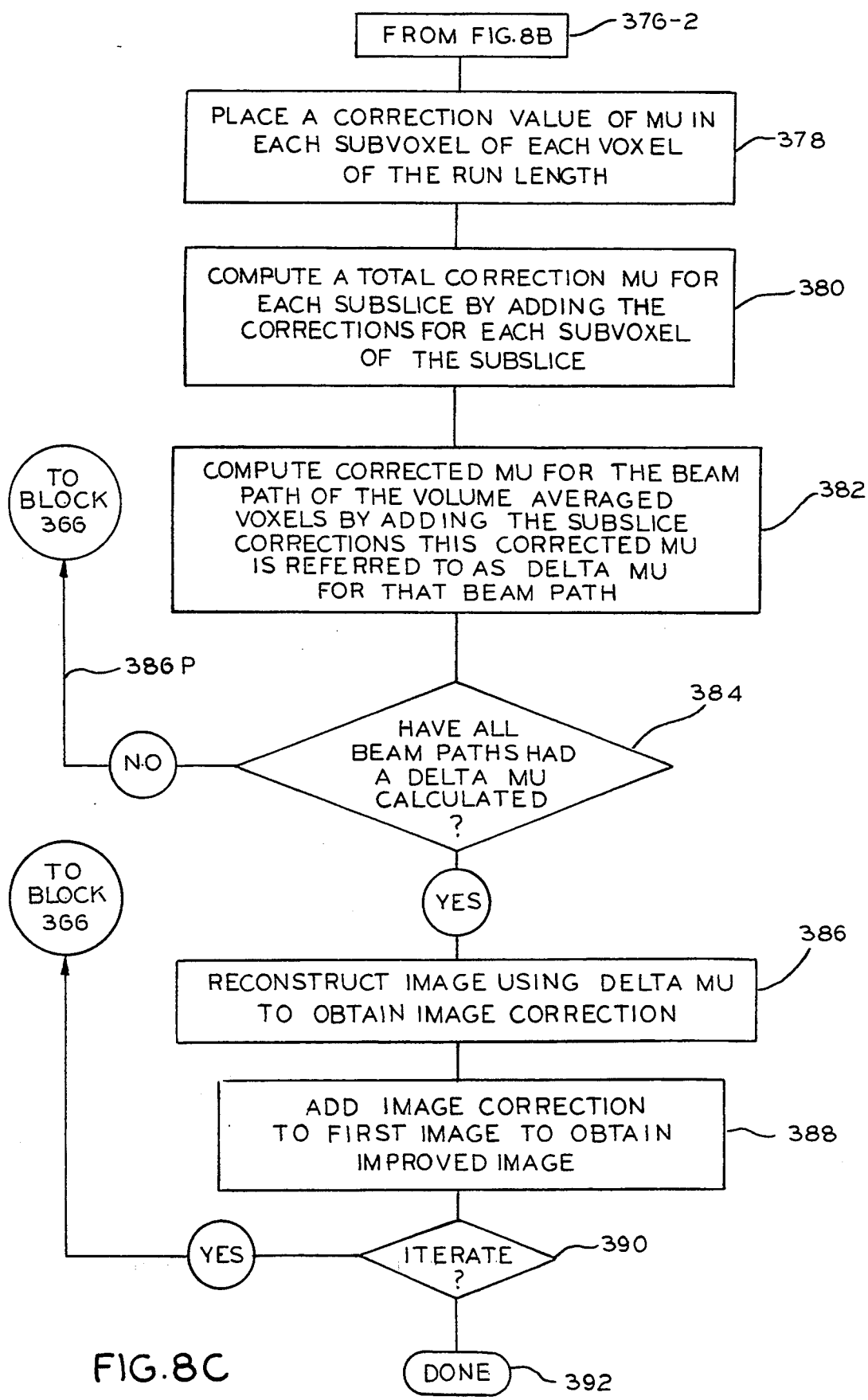

Turning now to FIGS. 8A, 8B, 8C, there is shown a flow chart showing the steps required to compute an improved image in accordance with the invention.

At block 360 $\mu$ is measured for a set of X-ray beams in a slice through a subject. The subject may be a person, a patient, or may be any physical object. For example, the object may be a casting, and it is desired to detect any flaws, if any, by X-ray tomography scanning.

At block 362 an image is reconstructed from the X-ray attenuation values measured at block 360. Appendix A gives a discussion of standard techniques for image reconstruction. This reconstruction gives a first image. At block 364-1 the computation proceeds to FIG. 8B at block 364-2.

At block 364-2 of FIG. 8B, the computation proceeds to bloc 366. At block 366 the computation first chooses an X-ray beam ray path. At block 368 the computation proceeds to search along the beam ray path chosen in block 366 in order to locate a run length of voxels. The run length is identified as a group of contiguous voxels having X-ray attenuation $\mu$ values in a range between that of a high attenuation material and a low attenuation material. In the example of a study of a patient's head, the high attenuation material is skull bone, and the low attenuation material is soft tissue such as brain tissue. In the example of a casting, the high attenuation material may be a metal, and the low attenuation material may be water of a water bath into which the casting is immersed for the purpose of conducting an X-ray tomographic study.

At block 370 the run length of volume averaged voxels located at block 368 is divided into subslices. The subslices are parallel to the X-ray beam path, and so the subslices subdivide voxels of the slice containing the X-ray beam path. The part of a voxel in a subslice is called a subvoxel. Accordingly, each voxel of the run length is divided into subvoxels by the subslices.

At block 372, compute a Z/h value for the run length of volume averaged voxels, using Equation EQ 5.

At block 374 place $\mu(1)$ or $\mu(2)$ in selected subvoxels of each voxel of the run length of volume averaged voxels. The fraction of subvoxels having $\mu(1)$ is given by the value of Z/h. Likewise, the fraction of subvoxels having material of $\mu(2)$ is given by $1-Z/h$. Accordingly, each voxel of the run length has the same arrangement of $\mu$ in its subvoxels. The slices above and below the current slice are used to arrange the high attenuation material in the upper part of a voxel, or in the lower part of the voxel.

Figure 8D:
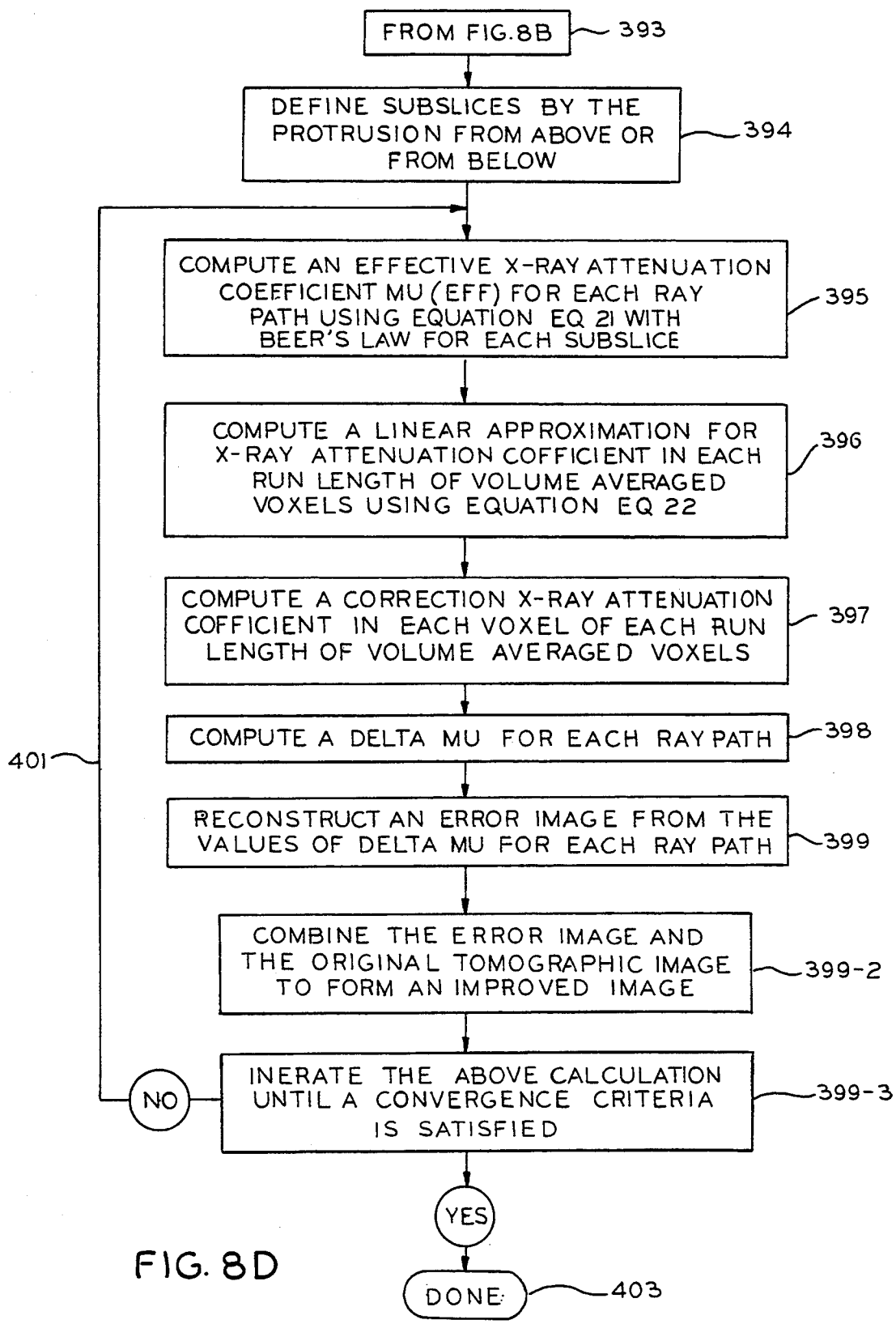

At block 376-1, the computation moves to FIG. 8C, at block 376-2, for the first exemplary embodiment of the invention, and moves to block 393 of FIG. 8D for the second exemplary embodiment of the invention.

Continuing the present discussion with the first exemplary embodiment of the invention, at block 378 a correction value of is placed in the subvoxels of each voxel of the run length, as the correction value is needed in order to achieve the computed value of Z/h of the run length of voxels.

At block 380 compute a correction $\mu$ for each subslice. Equation EQ 18 may be used, and the right hand side is evaluated using the values of $\Delta\mu$ and d for each run length of voxels. The correction to $\mu$ is then given as $\mu$(correction).

At block 382 compute a total correction value of X-ray attenuation $\mu$ for the beam ray path, by adding each of the $\mu$(correction) values calculated along a ray path through each subslice. In many cases, such as illustrated in FIGS. 10A, 10B, 10C, only one subslice will contribute to the total correction.

The total correction value is computed for an X-ray beam ray path by adding all of the correction values for the subslices.

At block 384, determine whether or not all of the beam ray paths have been corrected. If not, branch along path 386 to begin again at block 366 to choose another beam ray path. If all of the X-ray beam ray paths have had a correction value $\mu$(correction) computed, then proceed to block 386.

At block 386 the plurality of correction values $\mu$(correction) are used to reconstruct a correction image. The same computational procedure is used, as was used in block 362 in order to obtain the first image.

At block 388, add the image correction computed at block 386 to the first image computed at block 362 in order to obtain an improved image.

At block 390 a test is done in order to determine if the correction calculation should be repeated, that is iterated. If the result is "yes", iterate, then the computation takes path 386 to block 366 where the calculation is restarted, by choosing a first beam ray path. In the event that the determination at block 390 is "no", do not iterate, then the computation branches to block 392 where the computation ends. The improved image computed at the last execution of block 388 is then the output of the calculation.

The test at block 390 as to whether the iteration is complete is based on two criteria. The first criterion is whether the number of subslices is optimum. The second criterion is whether the total squared fractional change in X-ray attenuation has changed by less than a predetermined value from a chosen iteration to a next iteration.

In one embodiment, a number of subslices is chosen. For example, the number of subslices is chosen as ten (10) subslices. The $\Delta\mu$ values for each ray path are computed, based on the chosen subslices. The corrected ray path values of X-ray attenuation data are then computed. The corrected X-ray attenuation data are then used to compute another set of $\Delta\mu$ values. The change in the total squared change in X-ray attenuation is then computed, and the convergence of the value is tested. In the event that convergence is slow, or there is divergence, then the number of subslices is increased. This sequence of calculations is continued until the number of subslices and the number of iterations results in the smallest value of total squared change in X-ray attenuation results. The total squared change in X-ray attenuation from a chosen iteration to a next iteration is defined as X, where X is computed by the equation:

$$X = \sum_{\substack{\text{all ray} \\ \text{paths}}} (\Delta\mu/\mu)^2 \qquad \text{Equation EQ 19}$$

The total squared change in X-ray attenuation X is a function of two variables, the number of subslices and the number of iterations of the correction calculation. Accordingly, X may be written as:

X(number of subslices, number of iterations)

In an exemplary embodiment of the invention, X(number of subslices, number of iterations) is minimized by repeated choices of the number of subslices and the number of iterations. The number of iterations is determined by a failure of the next iteration to reduce X by more than a predetermined amount.

In a further exemplary embodiment of the invention, the number of subslices is changed in order to achieve convergence of iterations. The number of subslices may be further changed in order to improve rapidity of convergence of iterations. Convergence means that the value of X becomes smaller with the next iteration.

Turning now to FIG. 9, there is illustrated a beam ray path 400 through a skull 402. Run length 404 is composed of voxels which are volume averaged between bone and soft tissue. Run length 406 is composed of voxels which intercept three materials, soft tissue, bone, and a water bath. Region 422 is filled with a water bath in order to exclude air from the reconstruction. The water bath is used to prevent volume averaging over air, which would result in volume averaging over three materials. Volume averaging over three very different materials, such as air, water, and bone, would complicate the correction of the image reconstruction.

The voxels of run length 406 are accordingly, volume averaged over substantially two materials, water from the water bath in region 422, bone in region 410, and soft tissue in region 412. Run length 420 is composed of voxels which are volume averaged between water in region 422 and bone in region 424. Accordingly, the high attenuation material projects into the bottom of the voxels, and this point is determined by looking at the slices above and below the current slice.

It is known that the image was taken of a patient's head. The general shape of a skull is well known. Accordingly, in tracing along beam ray paths it is possible to determine which voxels are outside of the skull and which voxels are inside the skull. Voxels outside of the skull may be assigned the X-ray absorption $\mu$ of water, based upon general knowledge of the shape of the skull.

FIG. 9B illustrates the Z/h value computed for each of the contiguous run lengths 404, 406, 420. First, examining run length 404, correction quantities are calculated for each subvoxel so that the subvoxels of region 430 contain bone and region 432 contain soft tissue.

Second, examining run length 420, correction quantities are computed for region 434 so that the subvoxels contain water, and corrections are computed for region 436 so that the subvoxels contain bone.

Third, the direction of bone growth is determined for each run length by the $\mu$ values for the slice above the slice of beam ray path 400, and the slice below beam ray path 400. Voxels 450 are assigned the $\mu$ value of water, voxels 452 are assigned the $\mu$ value of bone, and voxels 454 are assigned the $\mu$ values of soft tissue.

A ray path is traced through each subslice parallel to the beam ray path 400, and a corrected value of $\mu$ is computed for each subslice. The subslice corrections to $\mu$ are used to compute a single $\mu$(correction) for the beam ray path 400.

Each beam path in the data used to reconstruct the image has a value of $\mu$(correction) similarly computed. The values of $\mu$(correction) for each beam path are then used to reconstruct a correction image. The correction image is combined with the original reconstructed image in order to obtain an improved image, as shown in the flow chart of FIGS. 8A, 8B, 8C.

Turning now to FIGS. 10A 10B, and 10C, there is shown a typical example of the invention. Voxels 500-1, 500-2, . . . 500-15 lie along beam ray path 502. Skull 504 is composed of dense bone. Material interior to the skull is soft tissue. Subslices 510-1, 510-2, . . . 510-11 are constructed parallel to beam ray path 502. By way of example, subvoxel 500-12, 510-6 designated by reference numeral 512, contains bone. Subvoxel 500-7, 510-6, designated by reference numeral 514, contains soft tissue, etc.

A typical numerical example of computing corrected X-ray attenuation coefficients $\mu$ for subvoxels of a run length of voxels is next given. Once computed, the corrected $\mu$ values are used as input for an image reconstruction. Run length 520 of voxels 500-1, 500-2, 500-3, 500-4, 500-5, 500-6, 500-7, 500-8, 500-9, 500-10 are selected as volume averaged with bone and soft tissue, where the selection is done by tracing along beam ray path 502 and selecting voxels having $\mu(i,j)$ values between the value for bone and for soft tissue. Each voxel has, generally, a different value of $\mu(i,j)$ computed from the original image reconstruction. The average value of the $\mu(i,j)$ values of the voxels of run length 520 is computed by adding the $\mu(i,j)$ values for the voxels of the run length and dividing by the number of voxels, and the average value is represented by $\mu$(avg). The value of the X-ray attenuation coefficient for bone, $\mu(1)$, is assumed to be 0.4 cm(−1). The $\mu$ value for soft tissue $\mu(2)$ is assumed to be 0.2 cm(−1). It is assumed that the average value for the voxels, $\mu$(avg), is 0.28 cm(−1).

The voxels are each assumed to be 0.3 cm in length parallel to beam ray path 502. There are 10 voxels in the run length, and so the run length therefore has a length R of 3.0 cm.

The assumed value of $\mu$(avg) for the run length can be used to calculate the number of subvoxels assigned to bone and to soft tissue, based on the original image reconstruction, as follows. There are N subvoxels in a voxel, and N(B) are assigned to bone and N(ST) are assigned to soft tissue:

$$\mu(avg) = (N(B) \mu(1) + N(ST) \mu(2))/N$$

This expression gives for the number of subvoxels assigned to bone N(B):

$$N(B) = N(\mu(avg) - \mu(2))/(\mu(1) - \mu(2))$$

$$N(B) = N(0.28 - 0.2)/(0.4 - 0.2)$$

$$N(B) = N\, 0.40$$

Of the 13 subvoxels shown in each voxel of FIG. 10A, 0.4*13 or 5 subvoxels are assigned to bone, leaving 8 subvoxels assigned to soft tissue.

The image may then be corrected in accordance with the invention as follows. The value of Z/h for the run length 520 is computed from equation EQ 5 as follows, $$\begin{aligned} Z/h &= (\exp(0.20 - 0.28)3.0 - 1)/ \\ &\quad (\exp(0.2 - 0.4)3 + 1) \\ &= -0.213/(-.451) \\ &= 0.47 \end{aligned}$$

The number of subvoxels assigned to bone is given by (Z/h)*N, or 0.47*13=6 subvoxels. Of the 13 total subvoxels, the 7 remaining are assigned to soft tissue. The subvoxels are shown in FIG. 10B.

The upper subvoxels are assigned to bone and the lower subvoxels are assigned to soft tissue, based upon a comparison with $\mu$ values in voxels of the slice above and the slice below the current slice. Based on the computed value of Z/h, the upper 47%, or 6 subvoxels, of the 13 subvoxels are now assigned to bone, and the lower 53%, or 7 subvoxels, are assigned to soft tissue.

A correction value of $\mu$ is then assigned to each voxel. The correction value may be the number of subvoxels which must be reassigned to the higher X-ray attenuation material, or assigned to the lower value material.

Corrections to the original assignments of materials to subvoxels are then:
for bone assignment:

$$\begin{aligned} \text{correction} &= \text{invention assignment} - \text{original assignment} \\ &\quad 6\ \text{subvoxels} - 5\ \text{subvoxels} \\ &= 1\ \text{subvoxel} \end{aligned}$$

Accordingly, one (1) additional subvoxel in each voxel of run length 500 is assigned to bone. Likewise, one (1) fewer subvoxel is assigned to soft tissue.

Corrections to the subvoxel assignments in accordance with the invention are shown in FIG. 10C. Voxels 530 are shown in single hatching, and are the original assignment of bone to 5 voxels made by the original image reconstruction. Voxels, 532 are the additional voxels assigned to contain bone by the present invention. Voxels 534, shown with no hatching, contain soft tissue. Accordingly, in this example, there is one additional row of voxels 532 containing bone rather than containing soft tissue. The X-ray attenuation value for voxels 532 is, accordingly, increased from the soft tissue value of 0.2 cm(−1) to the bone value of 0.4 cm(−1).

The total X-ray attenuation $\mu$ for beam path 520 is computed by application of Equation EQ 18. Each run length has its $\Delta\mu$ computed as above. The values of $\Delta\mu$ are used, along with d(m), the lengths of the run lengths, in order to evaluate the right hand side of Equation 18. The value of $\mu$(correction) is then calculated by division by d(total), the total length of all of the run lengths.

A similarly corrected $\mu$ value is computed for each beam path of the original data, and with 180 angular measurements with 256 substantially parallel pencil beams per angular measurement, there are 180*256 or 46,080 values of $\mu$(correction) calculated.

The values of $\mu$(correction) are then used for reconstruction of a correction image, and the correction image is added to the original reconstructed image to form an improved image.

Second Exemplary Embodiment

In a second exemplary embodiment of the invention, the thickness of a subslice may be determined by the values of Z/h computed for each voxel. That is, each subslice may be of a different thickness, where the thickness is determined by the different Z/h values calculated for the voxels of the run length. This embodiment is further illustrated in FIG. 11A and FIG. 11B Turning now to FIG. 11A, there is shown a beam ray path 600. The search along beam ray path 600 found N run lengths 602, 604, 608, 610 of volume averaged voxels. Note that homogenous voxels (ones containing only one substance) are not shown for simplicity, and because they are not needed in determining the correction value for the ray path. Also note that the individual voxels comprising each run length of volume averaged voxels are not shown, for simplicity.

The first step in obtaining the correction image is similar to that of the first exemplary embodiment. An X-ray beam path is selected and scanned for voxels which have a CT value indicating that they are volume averaged. A sequence of contiguous voxels along a ray path are selected as a run length of volume averaged voxels. There may be several run lengths of volume averaged voxels along a ray path, as discussed more fully in conjunction with FIG. 13 hereinbelow.

The second step in obtaining a correction image is to compute a Z/h value for each run length using equation EQ 5. The Z/h value denotes the fractional protrusion of the higher attenuating material having X-ray attenuation $\mu$(1). R in equation EQ 5 is the length of the run length. Length 602-1 gives the R value for run length 602. Length 604-1 gives the R value for run length 604. Length 610-1 gives the value of R for run length 610, etc.

The third step in computing a correction image is to define subslices. Once all of the Z/h values have been computed, subslices are defined by the values of Z/h. A simple way to lay out the subslices is, for example, to re-order the run lengths 602, 604, 606, 608, 610 as follows. The N run lengths are reordered as shown in FIG. 11B.

In re-ordering the run lengths of volume averaged voxels, the material protruding into the voxels of the run length from above is determined. The protrusion from above is determined for each run length by examination of the slice above and the slice below the slice being investigated, the slice penetrated by beam ray path 600. Each run length 602, 604, 606, 608, 610 has assigned to it the material protruding from above, and that material can be either the high X-ray attenuation material having $\mu$(1), or can be the low X-ray attenuation material having $\mu$(2). The run length with the smallest protrusion from above, regardless of whether the material protruding from above has $\mu$(1) or has $\mu$(2), is placed closest to the entrance point of the X-ray beam. The run length with the largest protrusion from above is ordered closest to the exit point of the X-ray beam.

The length of the protrusion from above is given by Z/h when the material protruding from above is high X-ray attenuation material having $\mu$(1). The length of the protrusion from above is given by (1−Z/h) when the material protruding from above is low X-ray attenuation material having $\mu$(2).

The reordering allows N+1 subslices to be easily defined, as shown in FIG. 11B. The first subslice has thickness T(1) 620, the thickness of the first protrusion from above 630. The second subslice has thickness T(2) 622 the difference in protrusion 630 and the second protrusion 632. That is, the thickness of each succeeding subslice is the difference in protrusion from above of the run length to the left, and the next subslice. Because there are N run lengths of volume averaged voxels, there are N+1 subslices. The thickness of the N+1'th subslice is give T(N) 624, the difference between the height of the slice, and the protrusion from above of the N'th run length. Stated differently, the thickness of each subslice is the difference between protrusion depths from above of adjacent run lengths of volume averaged voxels. This choice of subslice thickness produces subslices which have no volume averaging in the subslice.

The fourth step in computing a correction image is to compute an effective X-ray attenuation coefficient $\mu$(eff) for each X-ray beam ray path. A correction value for the X-ray attenuation coefficient for volume averaged voxels is calculated for a selected X-ray beam ray path, such as ray path 600. The effective X-ray attenuation coefficient $\mu$(eff) is calculated by applying Beer's Law along each Subslice, in the direction of X-ray beam path 600, where Beer's Law is stated as:

$$I(R) = I(0) \exp - (\mu\ R) \qquad \text{Equation EQ 20}$$

Represent the attenuated intensity exiting the first subslice having thickness T(1) 620 as I(1), the attenuated intensity exiting the second subslice having thickness T(2) 622 as I(2), etc. Detector 640 is divided into regions by the subslices, and detector portion 640-1 detects I(1). Detector portion 630-2 detects I(2), etc. Assuming a unit intensity I(0) striking the row of run lengths of volume averaged voxels as shown in FIG. 11B, the effective value of X-ray attenuation coefficient for the set of all run lengths may be computed from the equation:

$$T(1)\ I(1) + T(2)\ I(2) + \ldots T(N+1)\ I(N+1) = \qquad \text{Equation EQ 21}$$

$$I(0) \exp - (\mu(\mathit{eff})\ R)$$

Here R is given by:

$R = R(1) + R(2) \ldots R(N)$, the total length of all run lengths volume averaged voxels along X-ray beam ray path 600.

Multiplication of the intensity values by the thickness T of the subslice accounts for the different thickness of the subslices.

Each value of I in equation EQ 21 is computed by tracing the X-ray beam ray path 600 along the respective subslice, and using Beer's Law, equation 20, for each run length of volume averaged voxels.

The fifth step in computing a correction image is to compute an error value for X-ray attenuation coefficient for the volume averaged voxels along each ray path, indicated by $\Delta\mu$(ray path).

Once the effective X-ray attenuation coefficient $\mu$(eff) is computed for the X-ray beam ray path 600 using equation EQ 21, the error in the X-ray attenuation coefficient given by the original image reconstruction is computed for each voxel.

The linear approximation for X-ray attenuation $\mu$(lin) is given by the protrusion values Z/h and (1−Z/h) by the equation:

$$\mu(lin) = \mu(1)\,(Z/h) + \mu(2)\,(1 - Z/h) \qquad \text{Equation EQ 22}$$

The value of $\mu$(lin) is the value of $\mu$ which the image reconstruction process should have assigned to each voxel found in a run length of volume averaged voxels. Since the reconstruction process did not put this value $\mu$(lin) in each voxel, the correction process attempts to assign this value of $\mu$(lin) to each voxel. The correction process may be thought of as a two step process, first the subvoxels have the correct values assigned thereto, and secondly an image reconstruction is performed to update the value of $\mu$ in each voxel. The update must be done through an image reconstruction calculation because the value of $\mu$ in one voxel is linked with the value in many other voxels by the image reconstruction calculation.

The error in the X-ray attenuation coefficient in each volume averaged voxel is represented by $\Delta\mu(i)$, where i refers to the voxel:

$$\Delta\mu(i) = \mu(lin) - \mu(eff) \qquad \text{Equation EQ 23}$$

The error $\Delta\mu(i)$ for each volume averaged voxel is summed for all voxels in the sequence of run lengths of volume averaged voxels, in order to give a single value for ray path 600. That is, for a ray path of the X-ray beam, the error in X-ray attenuation coefficient $\Delta\mu$(ray path) for all volume averaged voxels along the X-ray beam ray path, is given by:

$$\Delta\mu(\text{ray path}) = \sum_{\text{volume averaged voxels along that ray path}} \Delta\mu(i) \qquad \text{Equation EQ 24}$$

An error for a each ray path is then computed using the procedure leading to equation 24, and then using equation 24. In an example where there are 180 angular measurements with 256 parallel measurements at each angle, this leads to 46,080 values of $\Delta\mu$(ray path).

The sixth step in computing a correction image is to do a reconstruction calculation using the ray path error values in the X-ray attenuation coefficients. That is, the values of $\Delta\mu$(ray path) are then used to reconstruct a correction image. For example, any of the reconstruction methods mentioned in Appendix A may be used for the reconstruction.

Finally, the correction image is added to the original image to produce an improved image. The improved image is the desired result.

The calculational sequence may be stated succinctly as follows, using psuedo-code terminology:
Read in uncorrected image and adjacent slices;
For each projection angle theta
  Rotate the image to the next projection angle
  For each X-ray beam ray path (row) in the image
    Locate all of the volume averaged regions (run lengths)
    Calculate Z/h for each region
      (Equation EQ 5)
    Re-order the volume averaged regions
    Define subslices based on projections from above
    Calculate $\mu$(eff) for the entire ray path
      Equation EQ 21, with Equation EQ 20
    Calculate $\Delta\mu(i)$ for each volume averaged voxel
      (Equation EQ 23)
    Calculate total error $\Delta\mu$ for each ray path
      (Equation 24)
  Endfor
Endfor
Reconstruct ray path errors into a correction image
Improved image = uncorrected image + correction image This calculation may be iterated. The X-ray attenuation values in the voxels of the improved image may be used as starting values for repeating the calculation. The improved image then takes the place of the original image in the above steps, and a second improved image is produced by working through the steps. A criteria is established for ending the iteration. For example, such a criteria may be that the fractional squared improvement, summed over all volume averaged voxels is less than a predetermined value. As a second example, the value of X, as set out in equation EQ 19 may be used to end the iteration.

Turning now to FIG. 8D, the flow chart illustrates an example of the second exemplary embodiment of the invention. At block 394, subslices are defined by examining the protrusion from above the slice of interest, and the slice below the slice of interest. At block 395 an effective X-ray absorption coefficient $\Delta\mu$(eff) is calculated using equation EQ 21, and using Boor's law for each subslice. At block 396 a linear approximation for the value of $\mu$ in a run length of volume averaged voxels is computed, and applied to each voxel of the run length. At block 397 a correction value $\Delta\mu(i)$ is computed for each voxel. At block 398, for each ray path, a delta X-ray attenuation coefficient $\Delta\mu$ is calculated. At block 399 an error image is reconstructed using all of the $\Delta\mu$ values calculated for each X-ray beam ray paths. At block 399-2 the error image is added to the original tomographic image to form an improved image. At block 399-3 the calculation beginning at block 395, along path 401. When the iteration criteria is satisfied the calculation is done at block 403.

Additional Features of the Invention

Turning now to FIG. 12, there is shown a typical X-ray tomography scanner. Gantry 700 supports X-ray tube 702. collimator 704 produces many substantially pencil beams 706. Pencil beams 706 diverge, and so form a fan beam 707. Detector 708 has a separate detector 710-1, 710-2, . . . etc. for each pencil beam 706. X ray tube 702, collimator 704, and detector 708 are rotatably mounted in gantry 700 so that they rotate about axis 720.

Axis 720 passes through a selected line in head 722 of patient 724. Patient 724 is supported by slide 730. Slide 730 moves in ways 732 of stand 734. Slide 730 moves along the direction shown by arrow 736. Direction 736 is substantially parallel to the axis of rotation 720 of the gantry 700.

With the patient in one position, fan beam 707 defines a slice such as slice 140 or slice 142 shown in FIG. 2. By moving slide 730 along the ways 732, and holding slide 730 in a fixed position, fan beam 707 defines a series of slices substantially parallel to slices 140, 142.

Angle theta 740 is changed in fixed increments, such as for example 1 degree increments. A full set of fan beam transmission measurements are measured at each angle by detector 708. The transmission measurements permit calculation of the X-ray attenuation $\mu$ along each pencil beam. In an example, 180 measurements with theta changed by 1 degree are made for a slice 140, 142, and the transmission measurements are made along each pencil beam 706. In a further example, transmission measurements may be made at 360 angles separated by 1 degree increments, for a total number of measurements of 360 times the number of pencil beams 707. In first generation equipment there was only one pencil beam produced, and so the pencil beam had to be translated parallel to itself. In second generation equipment there were up to approximately 52 pencil beams 706 in fan beam 707. In third generation equipment there are up to approximately 511 pencil beams 706 in a fan beam 707, and in fourth generation equipment there are up to approximately 1088 pencil beams 706 in a fan beam 707.

The reconstruction calculation must take into account the geometry of the fan beams. The original reconstruction calculation used substantially parallel pencil beams which were defined substantially parallel to each other, and taken at, for example, 360 angular positions.

Computer 750 receives electrical signals from detector 708, and from X-ray beam strength monitors inside of collimator 704. The image of the slice of the patient is reconstructed by computer 750. The reconstructed image is presented on an imaging device 752, such as television monitor or a cathode ray tube. Also, printer 754 produces a hard copy 760 of the image of the slice. Hard copy image 760 may be produced photographically by printer 754. Alternatively, hard copy image 760 may be produced by a printer 754 such as a laser printer.

The image produced on imaging device 752 and the hard copy image produced by printer 754 are used by physicians to diagnose the condition of the slice of the patient which was imaged. The present invention improves the quality of the image produced on television monitor or printer 754, over the quality of the image produced by the ordinary image reconstruction methods as described in Appendix A.

Turning now to FIG. 13, theere is shown a cross sectional view of a skull 800. Skull 800 is composed of bone. Plate 802 is also composed of bone. For example, plate 802 may be part of a bone shell around the inner ears (not shown), where the outer ears 804, 806 are shown. As a further example, plate 802 may be bone structures surrounding the eyes (not shown). Brain tissue 808 occupies the interior of skull 800. X-ray data is taken so as to reconstruct an image of slice 810.

Rows of voxels in slice 810 form volume averaged run lengths of voxels. Voxels 812 form a first run length of volume averaged voxels, where bone grows into the volume averaged voxels from above. Voxels 814 form a second run length of volume averaged voxels, where the bone grows into the voxels from below. Voxels 816 form a third run length of volume averaged voxels where the bone grows into the voxels from below. Voxels 815 form a run length of voxels, where the bone of the skull grows into the voxels from above.

After a reconstruction of the image by standard methods, such as those discussed in Appendix A, a correction value of X-ray attenuation $\mu$ is computed for each X-ray beam ray path. Each run length of volume averaged voxels is treated, for example as illustrated above in FIG. 10A, FIG. 10B, and FIG. 10C. Once occupancy of subslices is established, then either the first exemplary embodiment or the second exemplary embodiment may be used to compute the $\mu$ correction for each ray path along a subslice 820. The $\mu$ correction values for each subslice 820 are then added to give the correction value for the X-ray attenuation coefficient along that particular X-ray beam ray path. After all X-ray beam paths have a correction value of $\mu$ calculated, then a correction image is reconstructed. The original reconstructed image and the correction image are then added to obtain an improved image.

Figure 14A:
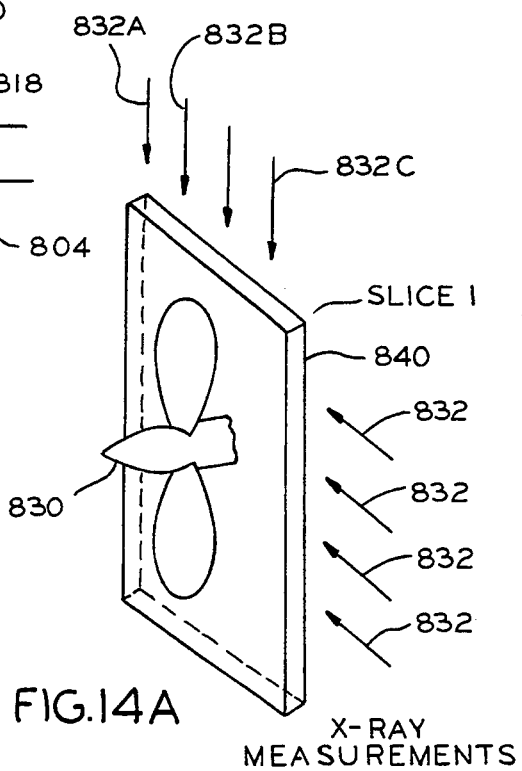

Turning now to FIG. 14A, there is shown an industrial object, such as a casting for a propeller. For example, propeller 830 may be of the type used in a boat. As further examples, propeller 830 may be of the type used in an airplane, as an impeller in a pump, as blades in a turbine or a jet engine, etc. Alternatively, propeller 830 represents any type of industrial object for which it is desirable to obtain an X-ray tomographic scan.

X-ray beam ray paths are illustrated by arrows 832. Enough X-ray transmission measurements are made along the ray paths 832 in order to enable reconstruction of an image in slice 840.

Figure 14B:
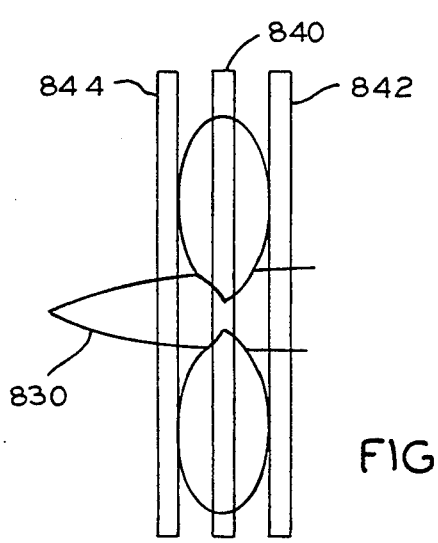

There is shown in FIG. 14B slice 840. Also shown in FIG. 14B are slice 842 to the right and slice 844 to the left of slice 840. Propeller 830 has a complex shape and so intersects all three slices 840, 842, 844 in complex patterns. Also, X-ray measurements are likewise made in slices 842, 844 in order to reconstruct an image in each of these slices.

Figure 14C:
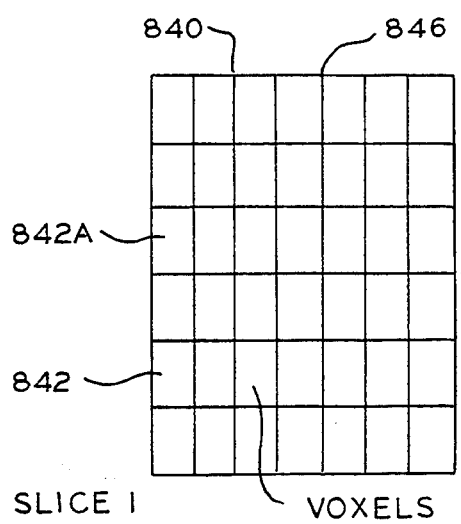

Turning now to FIG. 14C there is shown the voxels of slice 840. The voxels of slice 840 form rows 842 and columns 846.

Figure 14D:
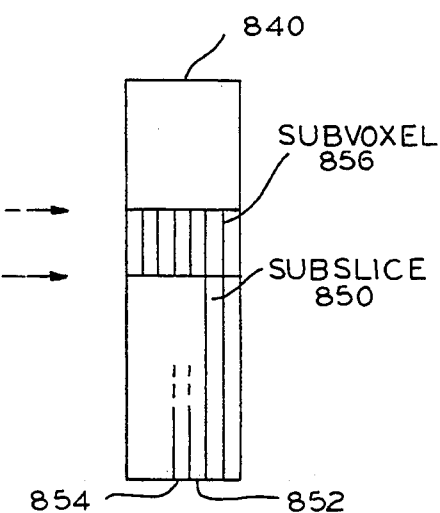

Turning now to FIG. 14D, there is shown an edge view of slice 840. In accordance with the invention, slice 840 is divided into a plurality of subslices, such as subslice 850. Other subslices 852, 854 are illustrated. Subslice 850 forms subvoxels with each row of voxels, such as row 842A. For example, subvoxel 856 is formed by the intersection of subslice 850 with row 842A of voxels. Because of the complex three dimensional shape of the industrial object, illustrated as propeller 830, there will be run lengths of volume averaged voxels formed in subslice 850. The high X-ray attenuation material may grow into volume averaged voxels from the left or from the right, or alternatively may grow into the slice from above or from below. In any event, each run length of volume averaged voxels has a corrected X-ray attenuation computed as was illustrated in FIG. 10 and accompanying discussion. Either the first exemplary embodiment or the second exemplary embodiment may be used to calculate a correction value for $\mu$ along each ray path. In the event that the first exemplary embodiment is used with Equation EQ 18 to compute a correction value for $\mu$ the calculation may be iterated in order to calculate the optimum number of subslices. A correction image is then reconstructed and added to the original reconstructed image in order to give an improved image.

When the volume averaged voxels have the high X-ray attenuation material growing into the run length of voxels from the side, as illustrated in FIG. 14D, the phenomena is referred to as an "edge gradient effect". The edge gradient effect is corrected by the present invention by using the volume averaged voxels to compute a correction value for the X-ray attenuation coefficient using, for example, either the first exemplary embodiment or the second exemplary embodiment.

Knowledge of the general shape of the object can be used to improve the calculation of the correction image. That is, from the general shape of the object, it can predicted whether the high X-ray attenuation material grows into the subvoxels from below or from above, or grows from the right or from the left. This "a priori" knowledge can be combined with searching the adjacent slices in order to improve the speed of the calculation.

A further source of "a priori" information to help speed the calculation is a three dimensional reconstruction developed from the original reconstructed image. In the event that X-ray data is taken for a number of slices, the original reconstructed image of each slice can be combined to develop a three dimensional image of the object. The three dimensional image can then be presented on imaging device 752 and printed on printer 754 (FIG. 12). The rough image from the original reconstructions can then be combined with knowledge of the object being imaged to assist in determining whether the volume averaged voxels have high X-ray intensity material growing in from the top or bottom, or from the left or the right. This use of a three dimensional image generated from the original reconstructed image may be used on skeletal areas such as the spine, the pelvis, the head, and also on industrial objects such as castings or plastic moldings, or any other object for which a tomographic image is desired.

APPENDIX A

Reconstruction calculational procedures are discussed in this Appendix because the present invention makes use of image reconstruction calculations. A description of three types of reconstruction algorithms are given by Albert Macovski in a chapter entitled "Principles of Reconstruction Algorithms", beginning at page 3877 of a book entitled "Volume 5, Radiology the Skull and Brain, Technical Aspects of Computed Tomography", edited by Thomas H. Newton and D. Gordon Potts, published by C. V. Mosby Company, 1981, all disclosures of which book are incorporated herein by reference.

A first type of reconstruction technique is referred to as an Algebraic Reconstruction Technique, or ART. This method is also called a "back projection". The purpose of the calculation is to compute a X-ray attenuation coefficient $\mu$ for each voxel, starting with the X-ray transmission measurements illustrated in FIG. 1 and FIG. 12. The calculation begins by assuming an arbitrary value for $\mu$ of each voxel, for example assume the value of zero for each voxel. Each ray sum is compared with that of the measured value. The difference is the cumulative error. The error is then uniformly distributed over all of the voxels along the ray. The calculation then Steps to another ray, and so proceeds through all rays of the measurements. A cumulative error for all of the rays is then computed.

The calculation is then repeated. A cumulative error for the repeated calculation is computed, and is expected to be smaller than the first cumulative error. The calculation is then repeated a number of times until the change in the cumulative error becomes less than a predetermined number. Once the change in cumulative error from one iteration of the calculation to the next iteration of the calculation becomes less than the predetermined number, the results of the calculation gives "the" calculated values for each voxel, $\mu$(calculated) and also referred to as $\mu(i,j)$ where i and j identify the row and column of the voxel in the slice 140, 142. The present invention calculates a correction, for volume averaging, to these values of $\mu$(calculated) obtained from the Algebraic Reconstruction Technique.

A second method of image reconstruction makes use of a two dimensional Fourier Transform. The measured values of X-ray transmission $\mu$ are used to estimate a Fourier transform of the true values of X-ray transmission of each Voxel. The Fourier transform is then processed by a numerical inverse transform computation. The inverse transform then gives the X-ray attenuation values $\mu$ for each voxel. The present invention then corrects these computed values of $\mu$ for volume averaging.

A third algorithm for image reconstruction uses results of theoretical Fourier transforms to produce a "filter". This filter is used in conjunction with the first method, the ART method. With the filter, the error between the ray sum of $\mu$ values is distributed un-evenly over the voxels of the ray, rather than evenly. This method is referred to as a filtered back projection.

What is claimed is:

1. An apparatus for correcting an X-ray tomographic image, where the tomographic image is created by measuring an X-ray transmission coefficient at each of a plurality of X-ray beam ray paths through an object to enable reconstructing a tomographic image of said object, comprising:

means for selecting a plurality of volume averaged voxels along at least one said X-ray beam ray path, and for placing contiguous volume averaged voxels in a runlength of volume averaged voxels, to make a plurality of run lengths of volume averaged voxels;

means for dividing said plurality of run lengths of volume averaged voxels into a plurality of subslices;

means, responsive to said plurality of subslices and responsive to said plurality of run lengths of volume averaged voxels, for computing a corrected value of X-ray attenuation coefficient for said X-ray beam ray path;

means for reconstructing a correction image using said corrected X-ray attenuation coefficient for each said X-ray beam ray path; means for obtaining an improved image by combining said tomographic image with said correction image.

2. An apparatus for correcting an X-ray tomographic image, comprising:

means for measuring an X-ray transmission coefficient at each of a plurality of X-ray beam ray paths through an object to enable reconstructing a tomographic image of said object;

means for reconstructing a tomographic image from said transmission data;

means for selecting a plurality of volume averaged voxels along at least one said X-ray beam ray path, and for placing contiguous volume averaged voxels in a run length of volume averaged voxels, to make a plurality of run lengths of volume averaged voxels;

means for dividing said plurality of run lengths of volume averaged voxels into a plurality of subslices;

means, responsive to said plurality of subslices and responsive to said plurality of run lengths of volume averaged voxels, for computing a corrected value of X-ray attenuation coefficient for said X-ray beam ray path;

means for reconstructing a correction image using said corrected X-ray attenuation coefficient for each said X-ray beam ray path;

means for obtaining an improved image by combining said tomographic image with said correction image.

3. The apparatus as in claim 1 further comprising:
means for determining an X-ray attenuation coefficient in a voxel in an upper slice above said slice of interest, and for determining an X-ray attenuation coefficient in a voxel in a lower slice below said slice of interest;

means, responsive to said determining said X-ray attenuation coefficient in said upper slice and responsive to said determining said X-ray attenuation coefficient in said lower slice, for ordering said subslices so that an upper subslice corresponds to a material in a voxel in said upper slice.

4. The apparatus as in claim 1 further comprising:
each said subslice has the same thickness.

5. The apparatus as in claim 1 further comprising:
a thickness of each said subslice is determined by a value of thickness of a first material, where said value of thickness of a first material is computed for said run length of voxels.

6. The apparatus as in claim 4 wherein said thickness of a first material is computed from Z/h values computed for each said run length of voxels.

7. The apparatus as in claim 1 wherein said means for computing a corrected X-ray attenuation coefficient for at least one selected subslice, further comprises;
means for choosing a material of selected X-ray attenuation coefficient to occupy a selected subvoxel.

8. The apparatus as in claim 7 further comprising:
means for computing a correction X-ray attenuation coefficient for a ray path along a subslice using equation 18.

9. The apparatus as in claim 7 further comprising:
means for computing a correction X-ray attenuation coefficient for a ray path along a subslice using the following equation, $$\sum_{i=0}^{N+1} T_i I_i = I_0 e^{-\mu_{eff} R}$$

where,
$T_i$ is the subslice thickness
$I_i$ is the intensity exiting the subslice
$I_0$ is the original unit intensity
$\mu_{eff}$ is the effective X-ray attenuation coefficient
R is the total run length, and
N is the number of subslices.

10. The apparatus as in claim 1 further comprising:
means for determining a shape of said object;
means, responsive to said shape, for selecting said subslices.

11. The apparatus as in claim 1 further comprising:
means for determining a shape of said object;
means, responsive to said shape, for selecting a material to occupy a selected subvoxel.

12. An apparatus for correcting an X-ray tomographic image, comprising:
 a. means for measuring an X-ray transmission coefficient at each of a plurality of X-ray beam ray paths through an object to enable reconstructing a tomographic image of said object;
 b. means for reconstructing a tomographic image from said transmission data;
 c. means for selecting at least one run length of volume averaged voxels along each said ray path;
 d. means for dividing said at least one run length of volume averaged voxels into a plurality of subslices;
 e. means, responsive to said plurality of subslices, for computing a corrected X-ray attenuation coefficient for each said ray path;
 f. means for repeatably computing a corrected X-ray attenuation coefficient for each said ray path by repeating step e, and for ending the repeated calculations when a convergence criteria is met;
 g. means for reconstructing a correction image using said corrected X-ray attenuation coefficient computed at step f for each said ray path;
 h. means for obtaining an improved image by combining said tomographic image and said correction image.

13. The apparatus as in claim 12 wherein said convergence criteria is X as computed by the following equation, $$X = \sum_{\text{all ray paths}} \left( \frac{\Delta \mu}{\mu} \right)^2$$

where,
$\Delta \mu$ is the change in X-ray attenuation coefficient,
$\mu$ is the X-ray attenuation coefficient.

14. The apparatus as in claim 12 further comprising:
means for selecting a new number of subslices;
means for comparing a value of said convergence criteria as computed with a first number of subslices and as computed with a second number of subslices, and for selecting as an optimum number of subslices a number of subslices yielding a smaller value of said convergence criteria.

* * * * *

UNITED STATES PATENT AND TRADEMARK OFFICE
CERTIFICATE OF CORRECTION

PATENT NO : 5,412,703
DATED : May 2, 1995
INVENTOR(S) : David J. Goodenough, et al.

It is certified that error appears in the above-identified patent and that said Letters Patent is hereby corrected as shown below:

On the title page, item [75] "Inventors", delete "Davil" and substitute therefore - - David - -.

Signed and Sealed this

Eighteenth Day of May, 1999

Attest:

Q. TODD DICKINSON

Attesting Officer

Acting Commissioner of Patents and Trademarks